(12) United States Patent
Snyder et al.

(10) Patent No.: US 7,147,468 B2
(45) Date of Patent: Dec. 12, 2006

(54) HAND HELD ORAL IRRIGATOR

(75) Inventors: Clifford J. Snyder, Fort Collins, CO (US); Gary L. Sokol, Longmont, CO (US); Roberta L. Callaghan, Fort Collins, CO (US)

(73) Assignee: Water Pik, Inc., Fort Collins, CO (US)

( * ) Notice: Subject to any disclaimer, the term of this patent is extended or adjusted under 35 U.S.C. 154(b) by 29 days.

(21) Appl. No.: 10/749,675

(22) Filed: Dec. 30, 2003

(65) Prior Publication Data

US 2004/0209222 A1 Oct. 21, 2004

Related U.S. Application Data

(60) Provisional application No. 60/437,300, filed on Dec. 31, 2002.

(51) Int. Cl.
*A61C 17/00* (2006.01)
(52) U.S. Cl. ....................................................... 433/80
(58) Field of Classification Search ................ 433/80, 433/82, 89; 601/162; 222/372, 381.1, 384, 222/385; 239/332; 607/2, 9, 11, 14, 17, 607/42
See application file for complete search history.

(56) References Cited

U.S. PATENT DOCUMENTS

| | | | |
|---|---|---|---|
| 555,588 A * | 3/1896 | Spencer | ....................... 137/858 |
| 1,933,454 A | 10/1933 | Sidney | |
| 2,783,919 A * | 3/1957 | Ansell | ........................ 222/211 |
| 2,794,437 A | 6/1957 | Tash | |
| 3,089,490 A | 5/1963 | Goldberg | |
| 3,096,913 A | 7/1963 | Jousson | |
| 3,209,956 A | 10/1965 | McKenzie | |
| 3,216,619 A | 11/1965 | Richards et al. | |
| 3,227,158 A | 1/1966 | Mattingly | |
| 3,370,214 A | 2/1968 | Aymar | |
| 3,391,696 A * | 7/1968 | Woodward | .................... 433/89 |
| 3,418,552 A | 12/1968 | Holmes | |
| 3,420,228 A | 1/1969 | Kalbfeld | |
| 3,496,933 A | 2/1970 | Lloyd | |
| 3,501,203 A | 3/1970 | Falk | |
| 3,522,801 A | 8/1970 | Robinson | |
| 3,536,065 A | 10/1970 | Moret | |
| 3,547,110 A | 12/1970 | Balamuth | |

(Continued)

OTHER PUBLICATIONS

US RE27,274, 01/1972, Mattingly (withdrawn)

*Primary Examiner*—Ralph A. Lewis
(74) *Attorney, Agent, or Firm*—Dorsey & Whitney LLP

(57) ABSTRACT

According to one broad aspect of one embodiment of the present invention, disclosed herein is a hand held oral irrigation device having a tip for dispensing fluids. In one example, an oral irrigation device includes a body portion, and a reservoir for storing fluids, wherein the body and/or the reservoir define a first major diameter at a lower end of the oral irrigation device, and define a second major diameter at an upper end of the oral irrigation device, the first major diameter being larger than the second major diameter. In this example, by providing such a geometry for the device, a user can grasp the device with one hand about the second major diameter during use. In another example, the body includes a pump for pumping fluids from the reservoir to the tip, wherein the pump includes an inlet valve and an outlet valve, the inlet valve including a reed valve made of flexible fabric material. The outlet valve may also include a reed valve made of flexible fabric material.

24 Claims, 18 Drawing Sheets

U.S. PATENT DOCUMENTS

| | | | |
|---|---|---|---|
| 3,572,375 A * | 3/1971 | Rosenberg | 137/512 |
| 3,578,884 A | 5/1971 | Jacobson | |
| 3,590,813 A | 7/1971 | Roszyk | |
| 3,636,947 A | 1/1972 | Balamuth | |
| 3,651,576 A | 3/1972 | Massa | |
| 3,768,472 A | 10/1973 | Hodosh et al. | |
| 3,783,364 A | 1/1974 | Gallanis et al. | |
| 3,809,977 A | 5/1974 | Balamuth et al. | |
| 3,827,147 A | 8/1974 | Condon | |
| 3,840,795 A | 10/1974 | Roszyk et al. | |
| 3,854,209 A | 12/1974 | Franklin et al. | |
| 3,874,506 A | 4/1975 | Hill et al. | |
| 3,912,125 A | 10/1975 | Acklin | |
| 4,001,526 A | 1/1977 | Olson | |
| 4,007,739 A | 2/1977 | Bron et al. | |
| D246,667 S | 12/1977 | Mackay et al. | |
| 4,060,870 A | 12/1977 | Cannarella | |
| 4,075,761 A | 2/1978 | Behne et al. | |
| 4,108,167 A | 8/1978 | Betush | |
| 4,108,178 A | 8/1978 | Betush | |
| 4,109,650 A | 8/1978 | Peclard | |
| 4,141,352 A | 2/1979 | Ebner et al. | |
| 4,144,646 A | 3/1979 | Takemoto et al. | |
| 4,154,375 A * | 5/1979 | Bippus | 222/325 |
| 4,160,383 A * | 7/1979 | Rauschenberger | 73/863.85 |
| 4,182,038 A | 1/1980 | Fleer | |
| 4,215,476 A | 8/1980 | Armstrong | |
| 4,219,618 A | 8/1980 | Leonard | |
| 4,227,878 A | 10/1980 | Lohn | |
| 4,229,634 A | 10/1980 | Hickman et al. | |
| 4,236,889 A | 12/1980 | Wright | |
| 4,249,899 A | 2/1981 | Davis | |
| 4,266,934 A | 5/1981 | Pernot | |
| 4,276,023 A | 6/1981 | Phillips et al. | |
| 4,276,880 A | 7/1981 | Malmin | |
| 4,302,186 A | 11/1981 | Cammack et al. | |
| 4,303,070 A | 12/1981 | Ichikawa et al. | |
| 4,319,568 A | 3/1982 | Tregoning | |
| 4,331,422 A | 5/1982 | Heyman | |
| 4,337,040 A | 6/1982 | Cammack et al. | |
| 4,340,365 A | 7/1982 | Pisanu | |
| 4,340,368 A | 7/1982 | Lococo | |
| D266,117 S | 9/1982 | Oberheim | |
| 4,363,626 A | 12/1982 | Schmidt et al. | |
| 4,365,376 A | 12/1982 | Oda et al. | |
| 4,374,354 A | 2/1983 | Petrovic et al. | |
| 4,382,167 A | 5/1983 | Maruyama et al. | |
| 4,382,786 A | 5/1983 | Lohn | |
| 4,412,823 A | 11/1983 | Sakai et al. | |
| 4,442,830 A | 4/1984 | Markau | |
| 4,442,831 A | 4/1984 | Trenary | |
| 4,452,238 A | 6/1984 | Kerr | |
| 4,454,866 A | 6/1984 | Fayen | |
| 4,512,769 A | 4/1985 | Kozam et al. | |
| 4,517,962 A | 5/1985 | Heckele | |
| 4,531,912 A | 7/1985 | Schuss et al. | |
| 4,531,913 A | 7/1985 | Taguchi | |
| 4,534,340 A | 8/1985 | Kerr et al. | |
| D283,374 S | 4/1986 | Cheuk-Yiu | |
| 4,585,415 A | 4/1986 | Hommann | |
| 4,591,777 A | 5/1986 | McCarty et al. | |
| 4,592,728 A | 6/1986 | Davis | |
| 4,602,906 A | 7/1986 | Grunenfelder | |
| 4,607,627 A | 8/1986 | Leber et al. | |
| 4,619,612 A | 10/1986 | Weber et al. | |
| 4,629,425 A | 12/1986 | Detsch | |
| 4,636,198 A | 1/1987 | Stade | |
| 4,644,937 A | 2/1987 | Hommann | |
| 4,645,488 A | 2/1987 | Matukas | |
| 5,125,835 A * | 6/1992 | Young | 433/80 |
| 5,150,841 A * | 9/1992 | Silvenis et al. | 239/332 |
| 5,197,460 A | 3/1993 | Ito et al. | |
| 5,286,192 A | 2/1994 | Dixon | |
| 5,716,007 A * | 2/1998 | Nottingham et al. | 239/332 |
| 6,030,215 A | 2/2000 | Ellion et al. | |

* cited by examiner

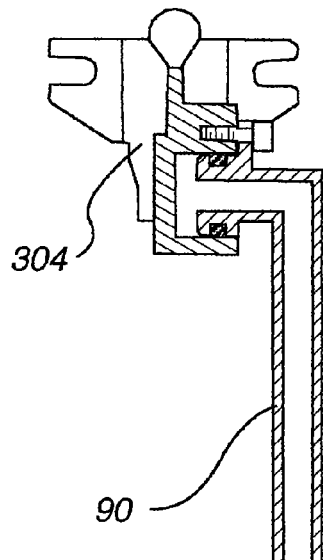
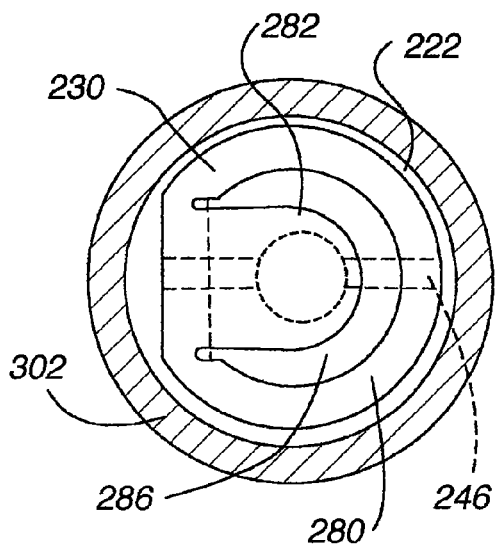
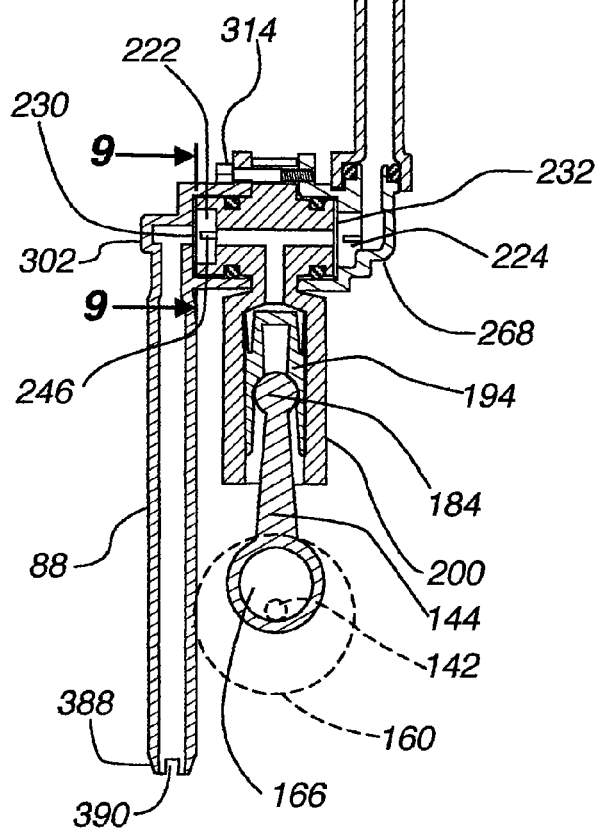
Fig. 7
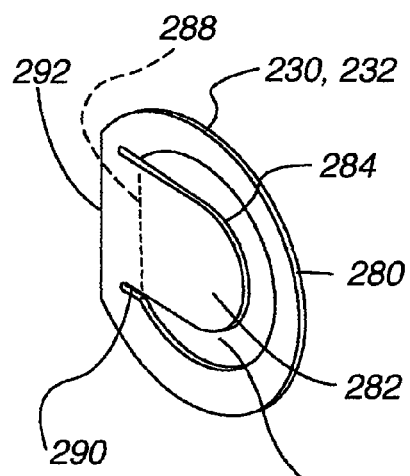
Fig. 8

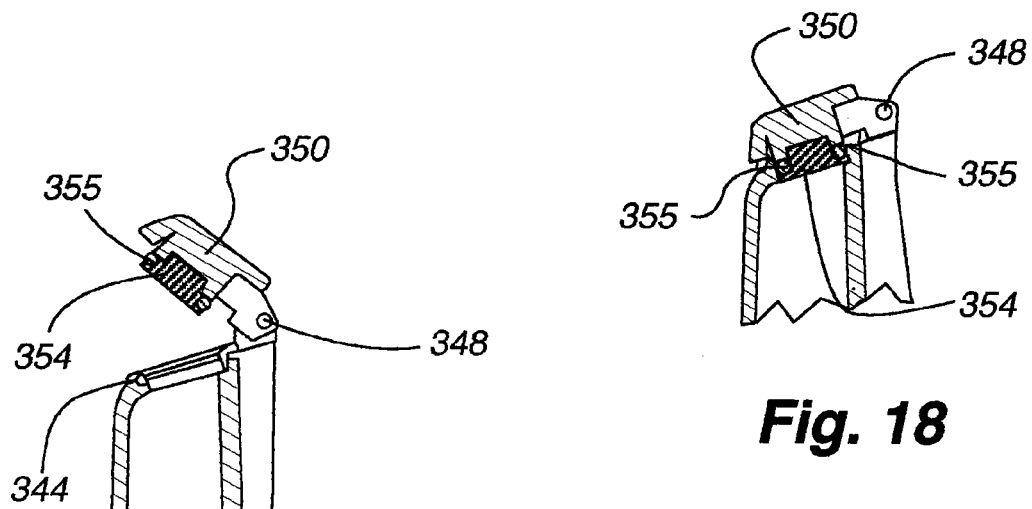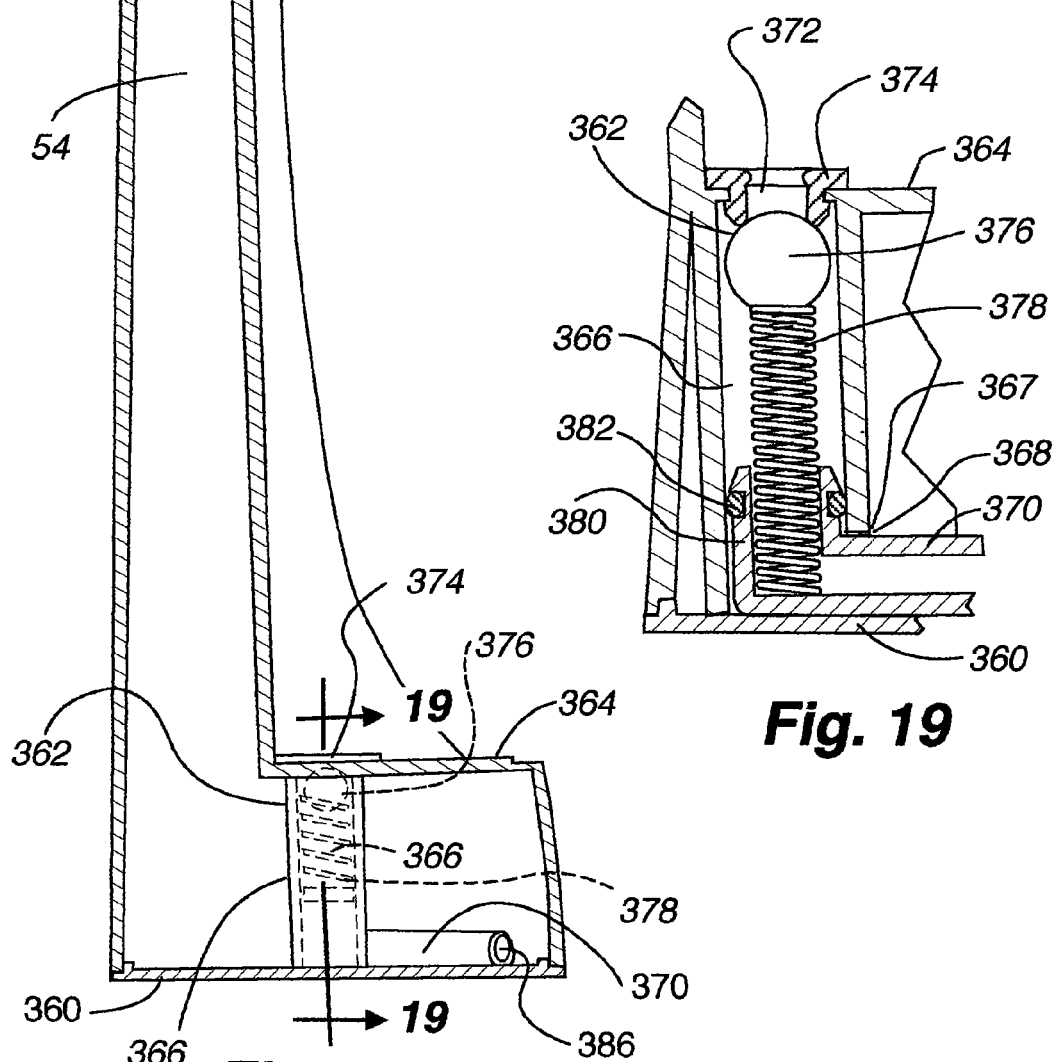

HAND HELD ORAL IRRIGATOR

CROSS REFERENCE TO RELATED APPLICATION

This application claims the benefit, under 35 U.S.C. § 119(e), of U.S. Provisional Patent Application No. 60/437,300 filed Dec. 31, 2002, entitled "HAND HELD ORAL IRRIGATOR" the disclosure of which is hereby incorporated by reference in its entirety.

FIELD OF THE INVENTION

This invention relates, in general, to devices for irrigating a person's teeth and gums.

BACKGROUND

Conventional oral irrigators typically include a large base unit having a reservoir, and a separate hand-held portion having a tip or wand that is connected to the reservoir with a tube. In use, a user directs fluid streams or pulses by pointing the tip of the hand-held portion in the desired position towards the users gum line. While the benefits of regular oral irrigation of the teeth and gums are well-known, oral irrigators having large base units can be difficult to transport, use, or store, for instance when the user is traveling, due to the size of the components.

As recognized by the present inventors, what is needed is a hand-held oral irrigator which is portable, easy to store and use, and provides a user with the benefits of oral irrigation of the teeth and gums. It is against this background that various embodiments of the present invention were developed.

SUMMARY OF THE INVENTION

According to one broad aspect of one embodiment of the present invention, disclosed herein is a hand held oral irrigation device having a tip for dispensing fluids. In one example, an oral irrigation device includes a body portion, and a reservoir for storing fluids, wherein the body and/or the reservoir define a first major diameter at a lower end of the oral irrigation device, and define a second major diameter at an upper end of the oral irrigation device, the first major diameter being larger than the second major diameter. In this example, by providing such a geometry for the device, a user can grasp the device with one hand about the second major diameter about the upper end during use. Other geometries are also possible.

In one example, the reservoir is detachable from the body so that a user can easily refill the reservoir. The reservoir may include an opening positioned at a top end, and a lid releasably secured about the opening. In one example, the reservoir has a capacity of approximately 120–200 ml of fluid.

In another example, the body may also include a motor, a pump, and a drive mechanism coupling the motor to the pump, the pump controllably delivering fluids from the reservoir to the tip. A three-way control structure may be provided having a first button for activating the motor, a second button for de-activating the motor, and a third button for releasing the tip from the body. Alternatively, an on/off control or switch may be utilized to activate and deactivate the motor.

The body may include a wall structure defining a first and second section within the body, the first section containing the pump and the second section containing the motor and the drive mechanism, wherein the first and second sections are fluidly isolated. In this way, the wall prevents fluids from reaching the motor and other electrical components within the second section in the body of the oral irrigation device.

In one example, the drive mechanism includes a pump gear coupled with the motor, wherein the pump gear includes an eccentric offset disc extending from the pump gear. A connecting rod may be coupled with the eccentric offset disc through a hollow cylindrical portion receiving the eccentric offset disc of the pump gear, and the connecting rod may include an arm extending from the cylindrical portion and a ball end positioned at the end of the arm. In this way, the eccentric rotation of the offset disc driven by the motor is converted into reciprocating motion of the connecting rod arm.

In another example, the pump may include a pump head having an inlet fluid port, an outlet fluid port, and an interior fluid channel in fluid communications with the inlet and outlet fluid ports; a pump body defining a cylindrical chamber in fluid communications with the interior fluid channel of the pump head; and a piston having a bottom portion and a top portion.

In one example, the inlet fluid port of the pump is positioned within the body at a location which is vertically lower than a location of the top or full level of fluid in the reservoir, thereby priming or self priming the pump with the fluid by force of gravity.

The bottom portion of the piston can receive the ball end of the connecting rod and the piston may be positioned within the cylindrical chamber of the pump body. In this way, the connecting rod drives the piston within the pump body to create suction/intake and compressing/exhaust cycles of the pump.

The body may include an inlet conduit fluidly coupling the reservoir with the inlet fluid port, and an outlet conduit fluidly coupling the outlet fluid port with the tip. The reservoir may include a fluid access valve fluidly coupling with the inlet conduit when the reservoir and the body are attached together.

The pump may also include an inlet fluid valve regulating fluid flow into the inlet fluid port, and an outlet fluid valve regulating fluid flow into the outlet fluid port, wherein as the piston is moved downwardly within the cylindrical chamber of the pump body, the inlet fluid valve is open, the outlet fluid valve is closed, and fluid is drawn from the inlet port (which is coupled with reservoir) into the cylindrical chamber of the pump body.

In another example, when the piston is moved upwardly within the cylindrical chamber of the pump body, the inlet fluid valve is closed, the outlet fluid valve is open, and fluid is expelled from the cylindrical chamber of the pump body to the outlet fluid valve for delivery to the tip.

In one embodiment, the pump of an oral irrigator includes at least one valve assembly having a reed valve therein. For instance, the inlet fluid valve may include a first reed valve made of flexible fabric material, and the outlet fluid valve may include a second reed valve made of flexible fabric material.

In one example, the reservoir may include a shelf portion defined about a bottom portion of the reservoir, and a base at the bottom end of the reservoir. The fluid access valve may also include a channel defined within the reservoir extending from the shelf to the base of the reservoir, the channel receiving the inlet conduit; a seal positioned about the top end of the channel; a spring extending upwardly from the base within the channel of the reservoir; a ball positioned within the channel between the seal and the spring; and a reservoir inlet conduit positioned along the base within the reservoir, the reservoir inlet conduit fluidly coupled with the channel so that fluid is drawn from the bottom of the reservoir. The spring presses the ball against the seal within the channel, and thereby prevents fluid from escaping the reservoir when the reservoir is separated from the body of the oral irrigator.

In another example, the oral irrigation device is provided with a mechanism for releasably securing a tip to the body of the oral irrigator. The tip may include an annular groove, and the body may include a tip holding structure having a cylindrical wall defining a cylindrical opening; a slot defined within the cylindrical wall; a clip having an interior lip, the interior lip positioned within the slot and extending into the cylindrical opening; and a spring for biasing the lip of the clip into the slot. In one example, when the spring is uncompressed and the tip fully inserted in the body, the lip is received within the annular groove of the tip and secures the tip to the body.

According to a broad aspect of another embodiment of the present invention, disclosed herein is a hand held oral irrigation device having a tip for dispensing fluids. In one example, the device includes a reservoir for storing fluids and a body including a pump for pumping fluids from the reservoir to the tip, wherein the pump includes an inlet valve and an outlet valve, the inlet valve including a reed valve made of flexible, non-porous fabric material. The outlet valve may also include a reed valve made of flexible, non-porous fabric material.

According to another broad aspect of another embodiment of the present invention, disclosed herein is a hand held oral irrigator including a reservoir and a body portion, the body portion containing a pump with a fluid inlet port. In one example, the pump inlet port is positioned within the body and the reservoir is shaped such that the top of the reservoir is vertically higher relative to the position of the fluid inlet port of the pump. In this way, when the reservoir is full or approximately full of fluid, the fluid level in the reservoir is higher than the position of the pump inlet port, and therefore the pump is self-priming or primed by the effect of gravity.

Other embodiments of the invention are disclosed herein. The foregoing and other features, utilities and advantages of various embodiments of the invention will be apparent from the following more particular description of the various embodiments of the invention as illustrated in the accompanying drawings and claims.

BRIEF DESCRIPTION OF THE FIGURES

FIG. 7 illustrates a sectional view taken along sectional lines 7—7 of FIG. 5 showing various components of the fluid flow path of the body portion of an oral irrigator, in accordance with an embodiment of the present invention.

FIG. 8 illustrates an example of a reed valve used in the pump, in accordance with an embodiment of the present invention.

FIG. 9 illustrates a sectional view taken along section lines 9—9 of the inlet port of the pump of FIG. 7, in accordance with an embodiment of the present invention.

FIG. 17 illustrates a cross sectional view of the reservoir taken along section lines 17—17 of FIG. 3 showing the reservoir lid in an open position and the fluid access valve in a closed position, in accordance with an embodiment of the present invention.

FIG. 18 illustrates a portion of the cross-sectional view of FIG. 17 showing the reservoir lid in a closed position, in accordance with an embodiment of the present invention.

FIG. 19 illustrates a cross-sectional view taken along section lines 19—19 of FIG. 17 showing the fluid access valve in detail, in accordance with an embodiment of the present invention.

DETAILED DESCRIPTION

Figure 1:
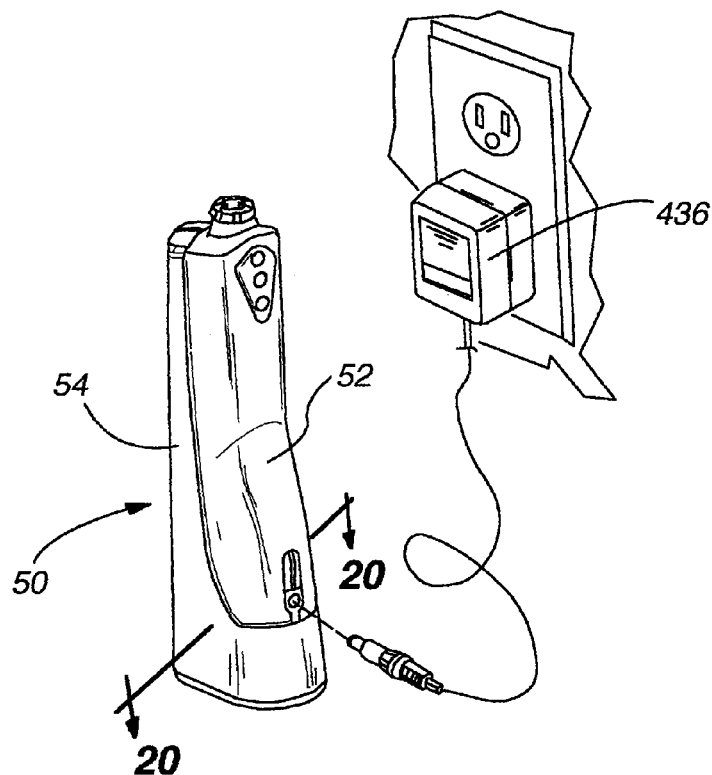
FIG. 1 illustrates a hand-held oral irrigator and a battery charger, in accordance with an embodiment of the present invention.
Figure 2:
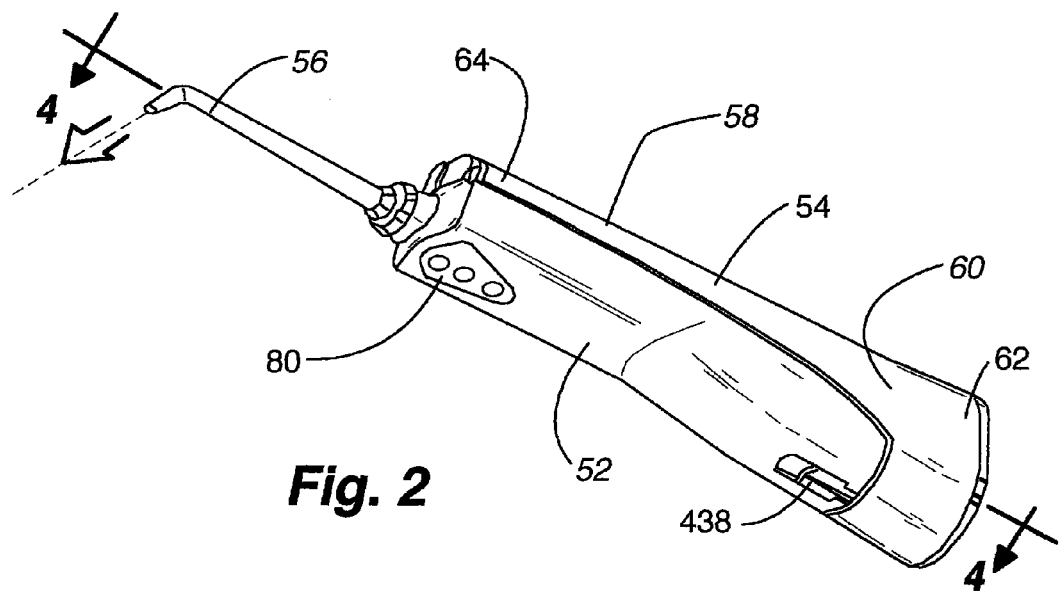
FIG. 2 illustrates a hand-held oral irrigator with a tip attached thereto, in accordance with an embodiment of the present invention.
Figure 3:
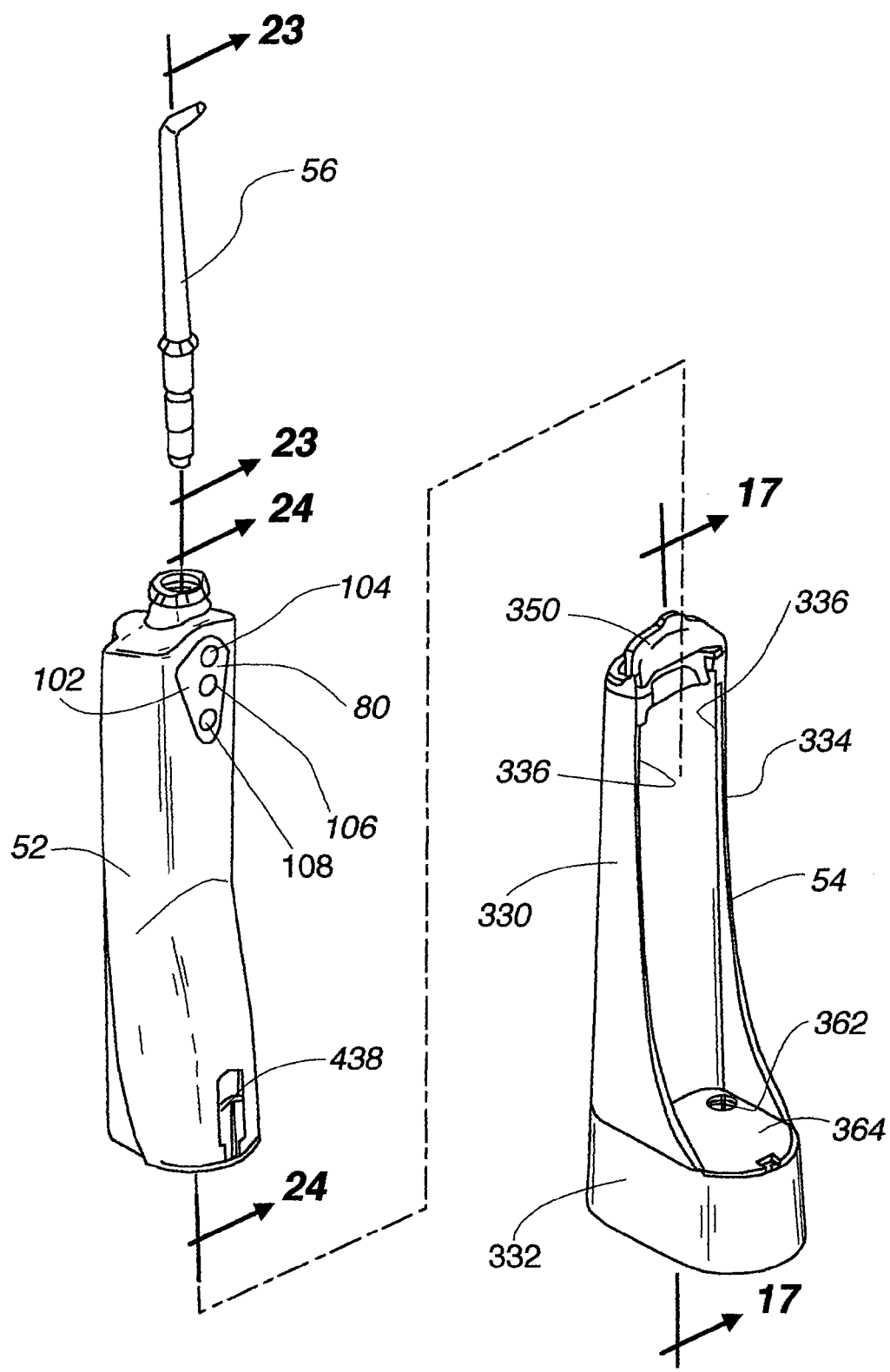
FIG. 3 illustrates an exploded view of an oral irrigator with a body portion, a detachable reservoir, and a detachable tip, in accordance with an embodiment of the present invention.
Figure 4:
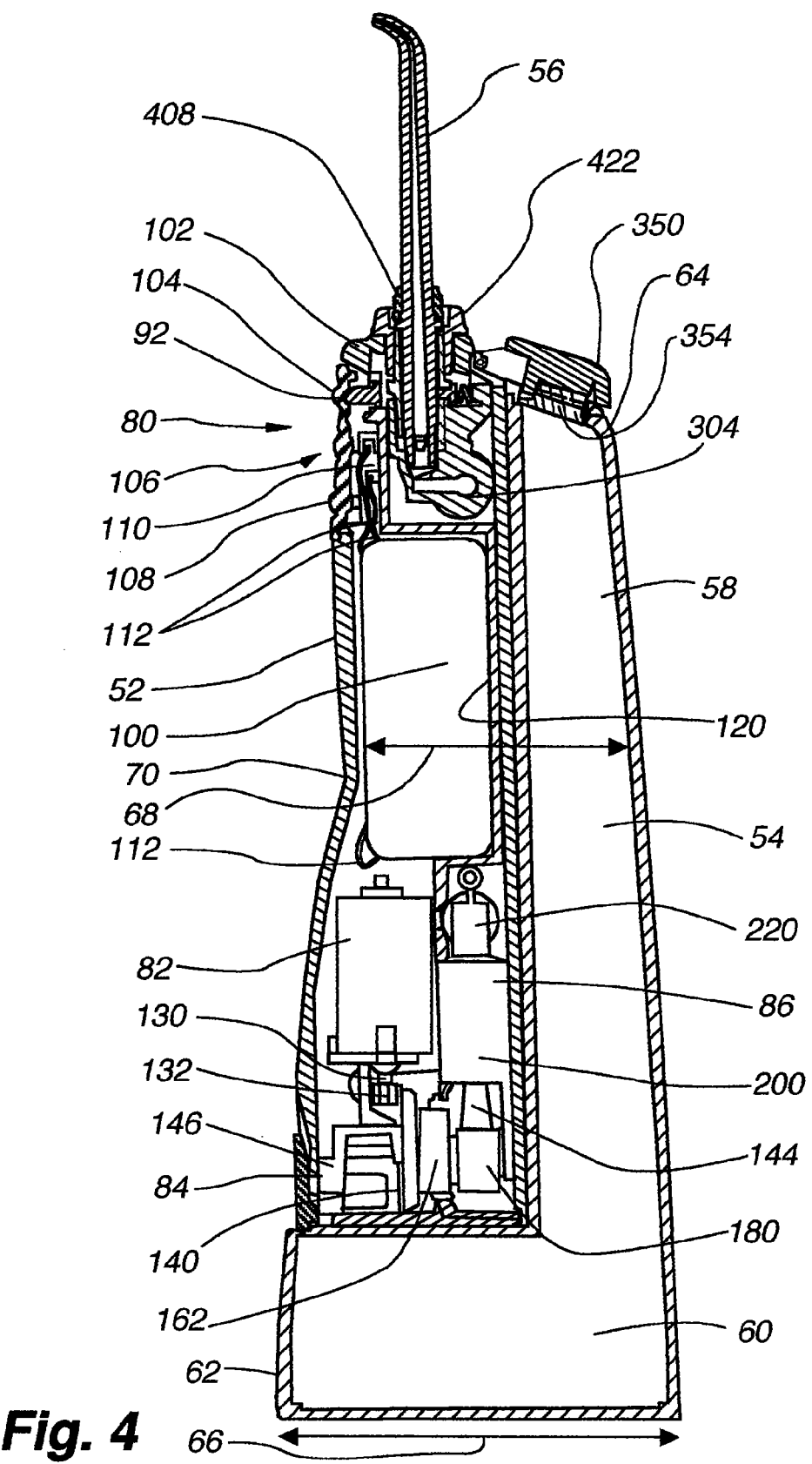
FIG. 4 illustrates a cross-sectional view taken along section lines 4—4 of the oral irrigator of FIG. 2, in accordance with an embodiment of the present invention.
Figure 20:
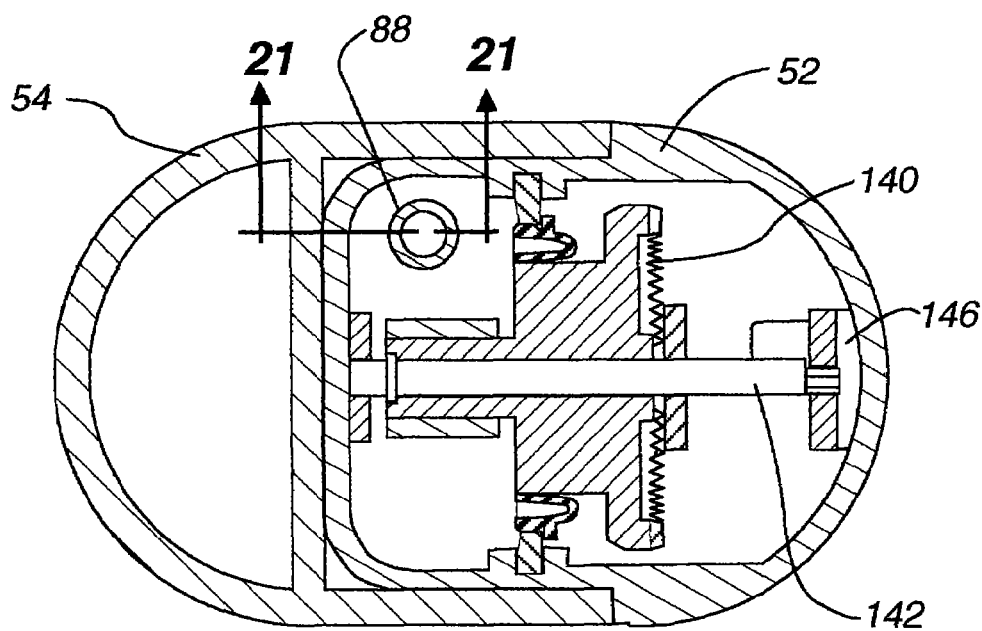
FIG. 20 illustrates a sectional view along section lines 20—20 of FIG. 1.

Disclosed herein are various embodiments of a hand held, compact and portable oral irrigator with a detachable and refillable reservoir, wherein various different tips may be attached to the oral irrigator. Referring to FIGS. 1–3, in one example, a hand-held oral irrigator 50 has a body 52, a detachable refillable reservoir 54 for storing fluid, and a detachable jet tip or nozzle 56 for delivering a pressurized stream of fluid to the user's teeth and gums. The body 52 and the reservoir 54 are shaped having a slender upper portion 58 so that a user can easily grasp the oral irrigator 50 about the upper portion 58, and a larger lower portion 60 which aids in the storage of fluids in the reservoir 54 as well as providing a stable platform when the oral irrigator 50 is placed on a table or surface in a vertical orientation. When coupled together as shown in FIG. 4, the body 52 and reservoir 54 form an oral irrigator 50 that has a generally oval cross-section from the lower end 62 (See FIGS. 4 and 20) to the upper end 64 (FIG. 4). At the lower end 62, the oral irrigator 50 has a larger major diameter 66 that decreases to a second, smaller major diameter 68 at a point 70 along the length of device 50, such as at a midpoint of the oral irrigator 50. The second major diameter 68 may be relatively consistent from point 70 to the upper end 64, or may increase if desired.

In one example, the reservoir 54 defines a larger major diameter 66 along the lower end 62 of the oral irrigator 50, while portions of the base 52 and reservoir 54 define a second diameter 68 being smaller than diameter 66. In one embodiment, the smaller diameter 68 defines a region about where a user may grasp or hold the oral irrigation device 50 during use.

Figure 5:
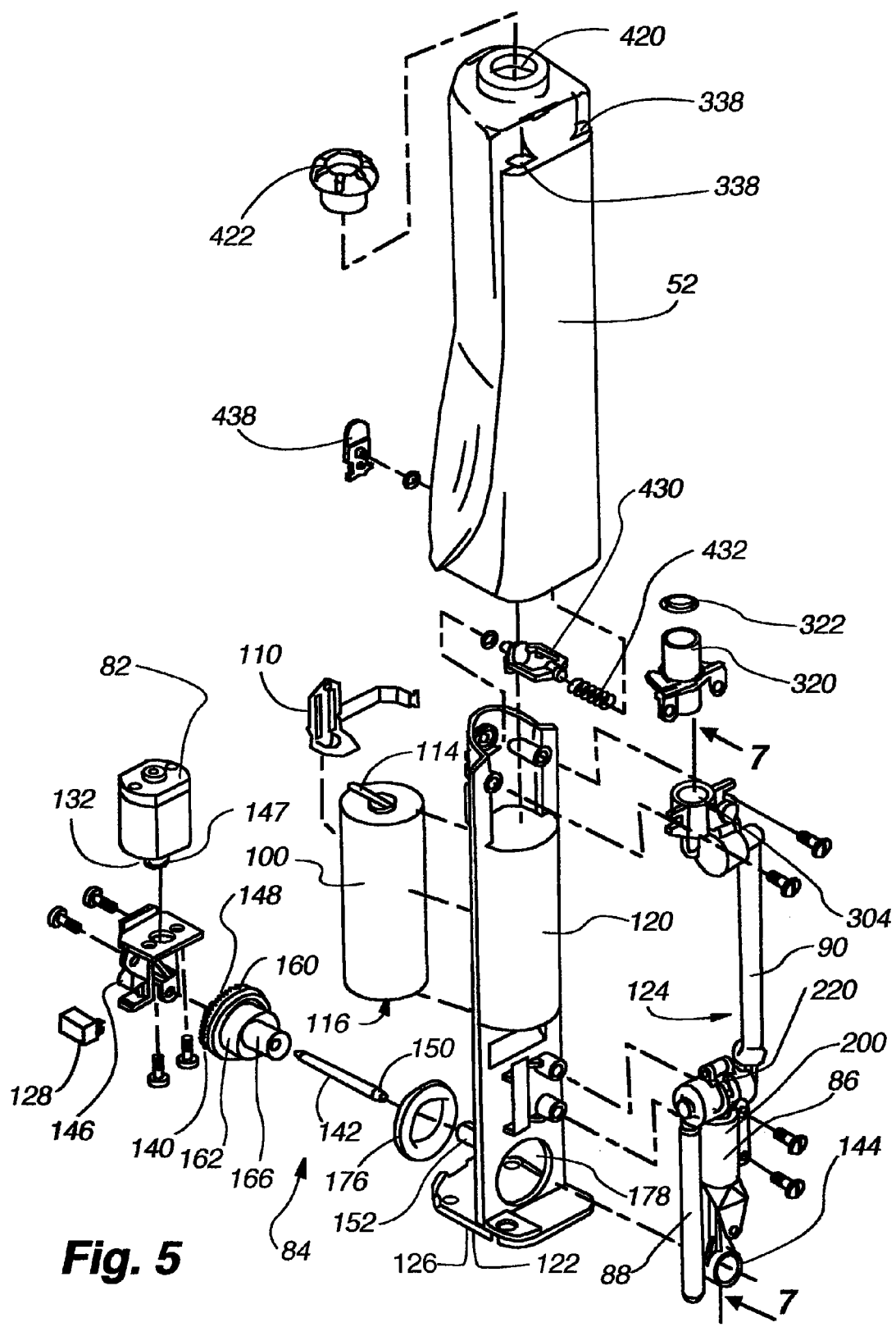
FIG. 5 illustrates an exploded view of the body portion of an oral irrigator, in accordance with an embodiment of the present invention.

Generally and as shown in FIGS. 4–5, the body 52 includes a three-way control structure 80 that permits the user to turn the oral irrigator 50 on or off or to release the tip 56 from the body 52, a motor 82, a drive mechanism 84, and a pump 86 connected to fluid conduits 88, 90 for drawing fluid from the reservoir 54 and delivering fluid to the tip 56. Alternatively, the body 52 may include an on/off control or switch to activate and deactivate the motor 52. The body 52 also includes a tip securing mechanism 92 (FIGS. 25, 26) that permits the user to releasably secure different tips to the body.

Figure 6:
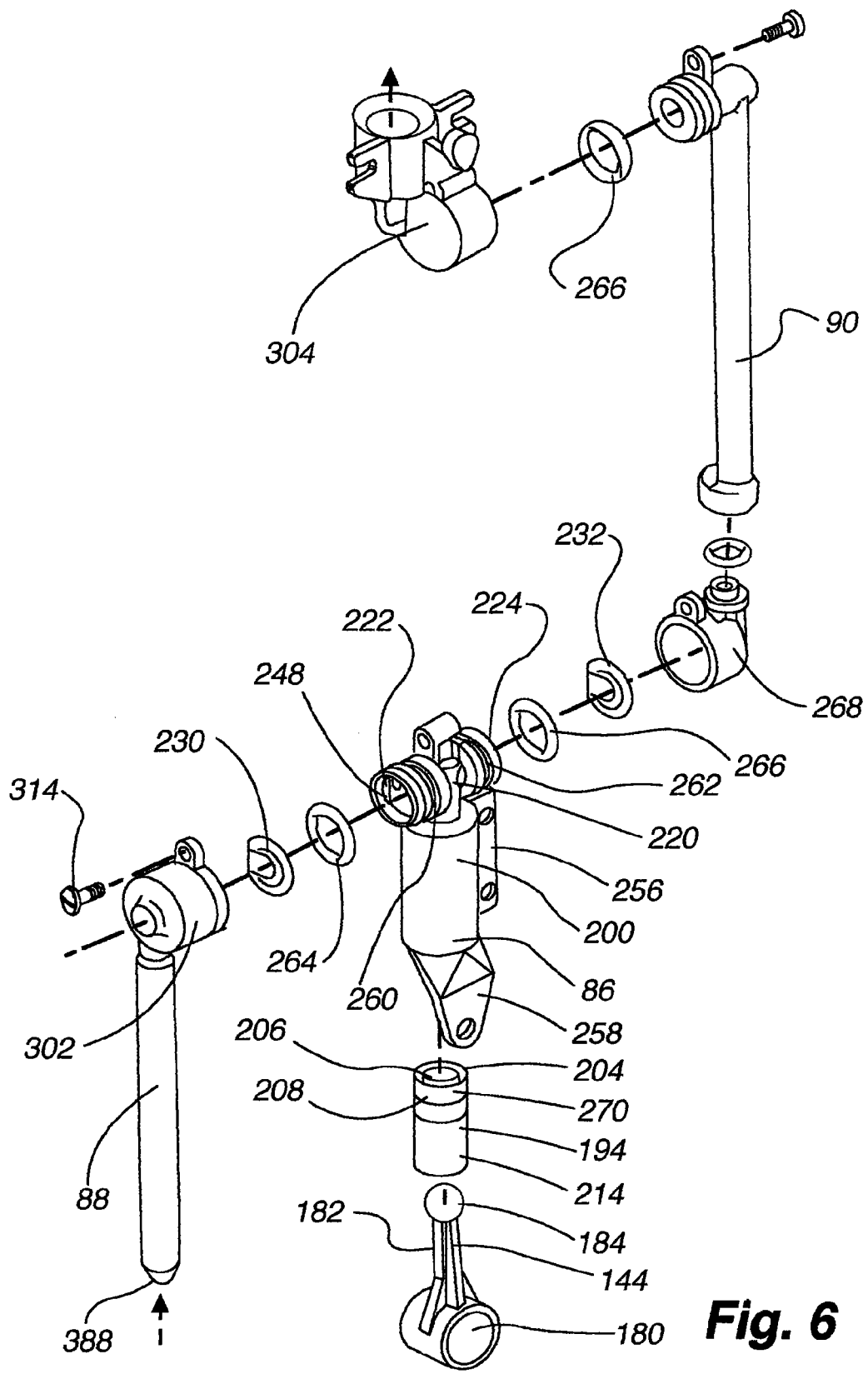
FIG. 6 illustrates various components of a fluid flow path of the body portion of an oral irrigator, in accordance with an embodiment of the present invention.

Referring to FIGS. 4–6, the body 52 generally includes a motor 82 and a rechargeable battery 100 that, based on the state of the control structure 80, activates a pump 86 through a drive mechanism 84 that draws fluid from the reservoir 54 and delivers the fluid to the tip 56 in a controlled and pressurized manner. In FIGS. 3–4, the control structure 80 includes a wedge shaped pad 102 with three buttons 104, 106, 108 integrated therein and adapted for depression by a user's thumb or finger. In one example, a first button 104 controls a tip release mechanism 92 (FIGS. 25, 26) for controlling the release of a tip 56 from the body 52; and a second button 106 and third button 108 selectively activate and deactivate an electrical switch or contact 110 connected through wires or conductors 112 to the positive and negative terminals 114, 116 of a rechargeable battery 100, thereby turning the oral irrigator on and off.

Referring to FIG. 5, the body 52 includes a wall structure 120 which defines a first section 122 of the interior of the body which is used to contain a self-contained fluid flow path 124 and related components, and a second section 126 of the interior of the body which is used to contain the motor 82, battery 100, charging connector 128, and other electrical components of the oral irrigator 50. The wall structure 120 maintains sections 122 and 126 isolated, which prevents fluid from entering section 126 and damaging motor 82, battery 100, or any other electrical components within section 126.

The battery 100 is electrically coupled with the motor 82 through wires 112 or other conductors. In FIG. 4, the motor 82 includes a shaft 130 that drives a motor gear 132. In one example, the motor 82 is a DC motor rotating at 8000–11200 RPM under no load conditions when 2.3 volts is applied.

Figure 24:
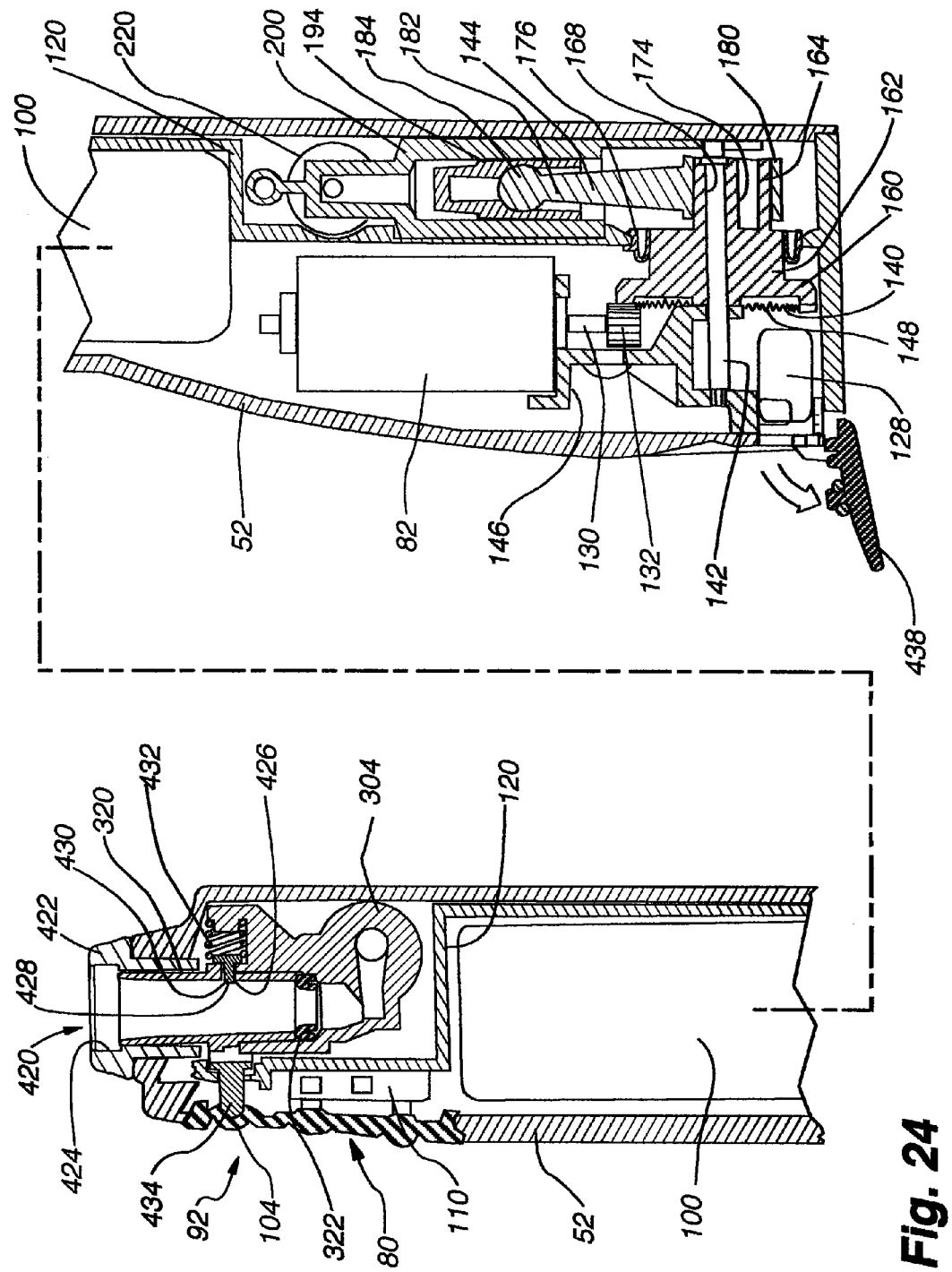
FIG. 24 illustrates a sectional view taken along section lines 24—24 of FIG. 3 of the body portion of a hand-held oral irrigator, in accordance with an embodiment of the present invention.

In FIG. 5, the motor gear 132 is operably connected with a drive mechanism 84 for driving the pump 86. In one example and as shown in FIGS. 5 and 24, the drive mechanism 84 includes a pump gear 140, a gear pin 142, and a connecting rod 144. A motor/gear support member 146 securably attaches the motor 82 and the gear pin 142 within the body 52 of the oral irrigator 50, and maintains a fixed orthogonal orientation between the motor 82 and the pump gear 140 so that the teeth 147 of the motor gear 132 are properly aligned with the teeth 148 of the pump gear 140. The opposing end 150 of the gear pin 142 may be secured to an interior portion of the body or to an extension 152 from the wall structure 120.

Figure 12:
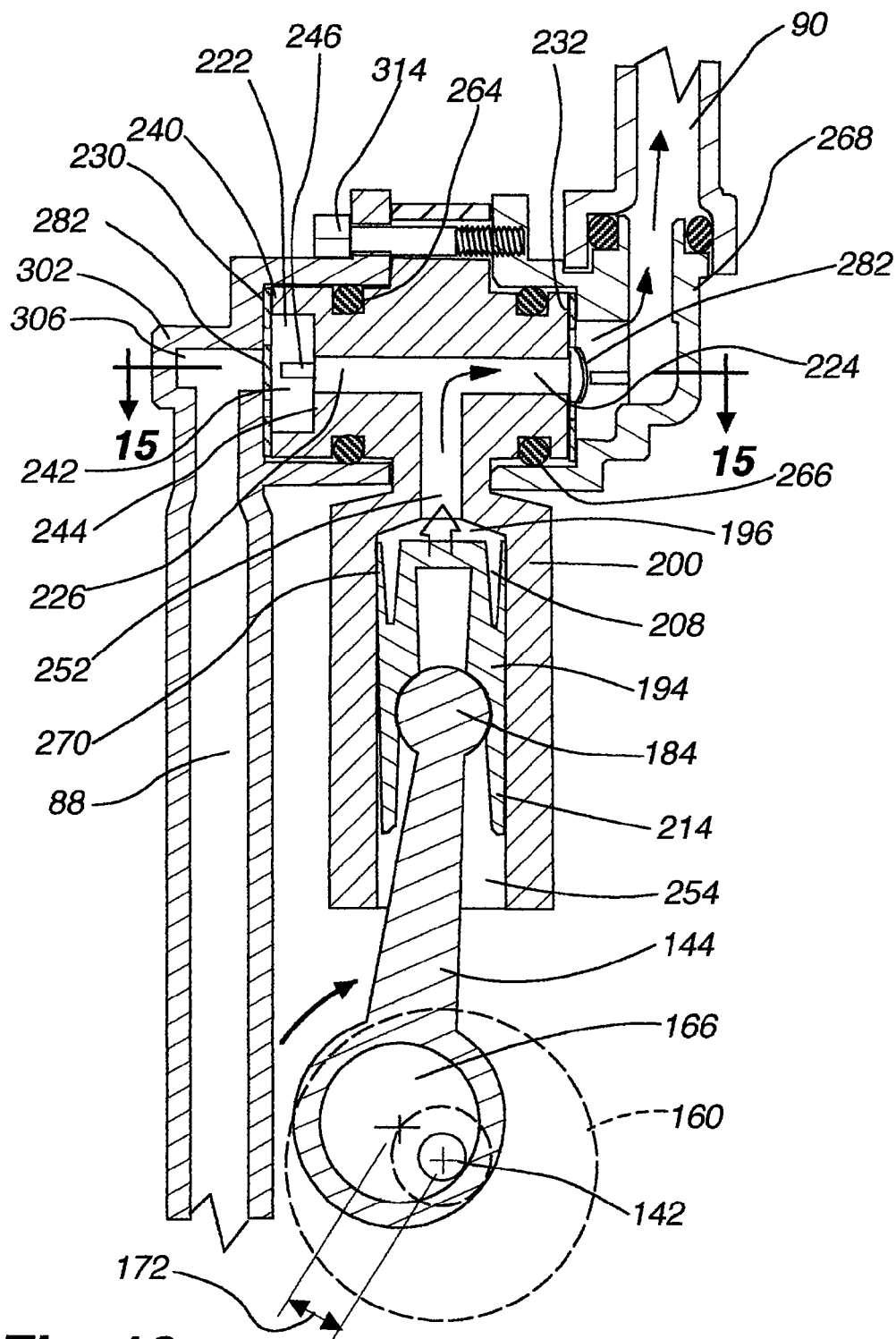
FIG. 12 illustrates a sectional view of the pump during an exhaust or compression stroke, in accordance with an embodiment of the present invention.
Figure 13:
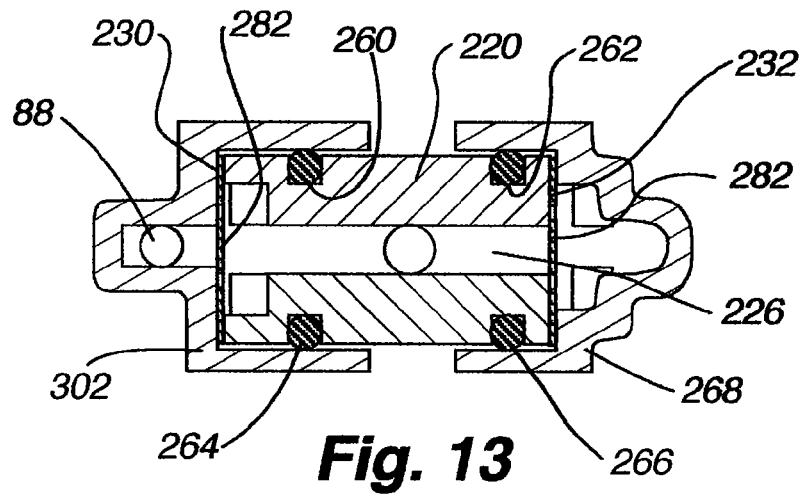
FIG. 13 illustrates a sectional view taken along section lines 13—13 of FIG. 10 showing the positions of the flaps of the reed valves, in accordance with an embodiment of the present invention.
Figure 30:
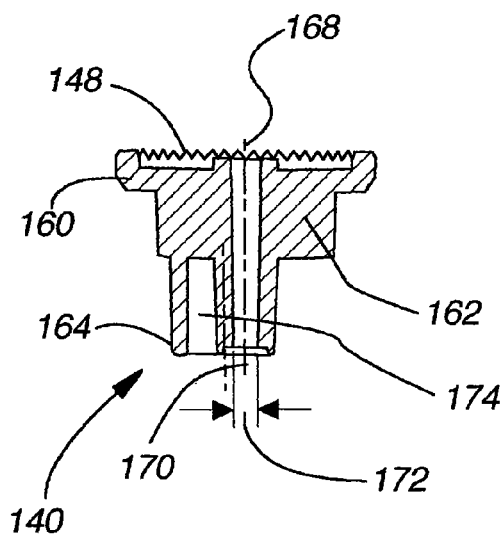
FIG. 30 illustrates a sectional view of a pump gear taken along section lines 30—30 of FIG. 27, in accordance with an embodiment of the present invention.
Figure 27:
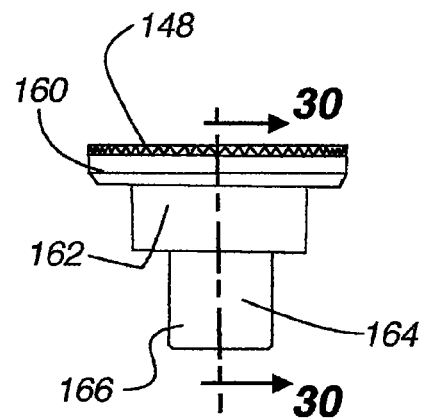
FIG. 27 illustrates a front view of a pump gear, in accordance with an embodiment of the present invention.
Figure 29:
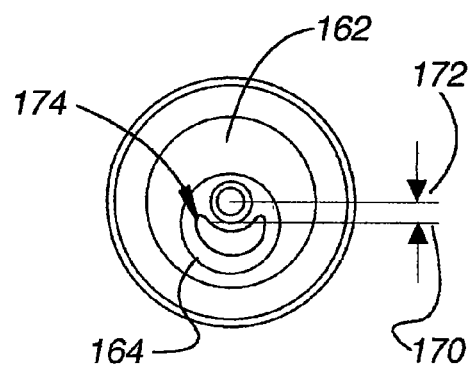
FIG. 29 illustrates a bottom view of a pump gear, in accordance with an embodiment of the present invention.

Referring to FIGS. 27–30, the pump gear 140 includes an outer disc 160 having the gear teeth 148 extending therefrom, an intermediate concentric disc 162, and an offset disc 164 which acts as an eccentric shaft 166, wherein the outer disc 160 and the concentric disc 162 are both centered about a cylindrical axis 168 through which the gear pin 142 is positioned and about which the pump gear 140 rotates. As shown in FIGS. 12 and 30, the center 170 of the offset disc 164 is offset from the cylindrical axis 168 by some offset distance 172, for example 0.081 inches or 0.091 inches. The amount of the offset distance 172 will vary depending upon the desired performance of the oral irrigator 50 as well as other design parameters such as the desired fluid pressure delivery, the mechanics of the pump 86, or the rotational speed of the motor 82. In one example, the eccentric offset disc 164 has a crescent shaped opening 174 therethrough in order to control the rotational inertia of the pump gear 140 as it rotates, as well as to simplify the manufacture of the pump gear 140. In FIG. 5, a seal 176 is positioned between the pump gear 140 and the wall structure 120 about an opening 178 in the wall structure 120 to prevent any moisture from entering the second section 126 from the first section 122 about the pump gear 140.

Figure 10:
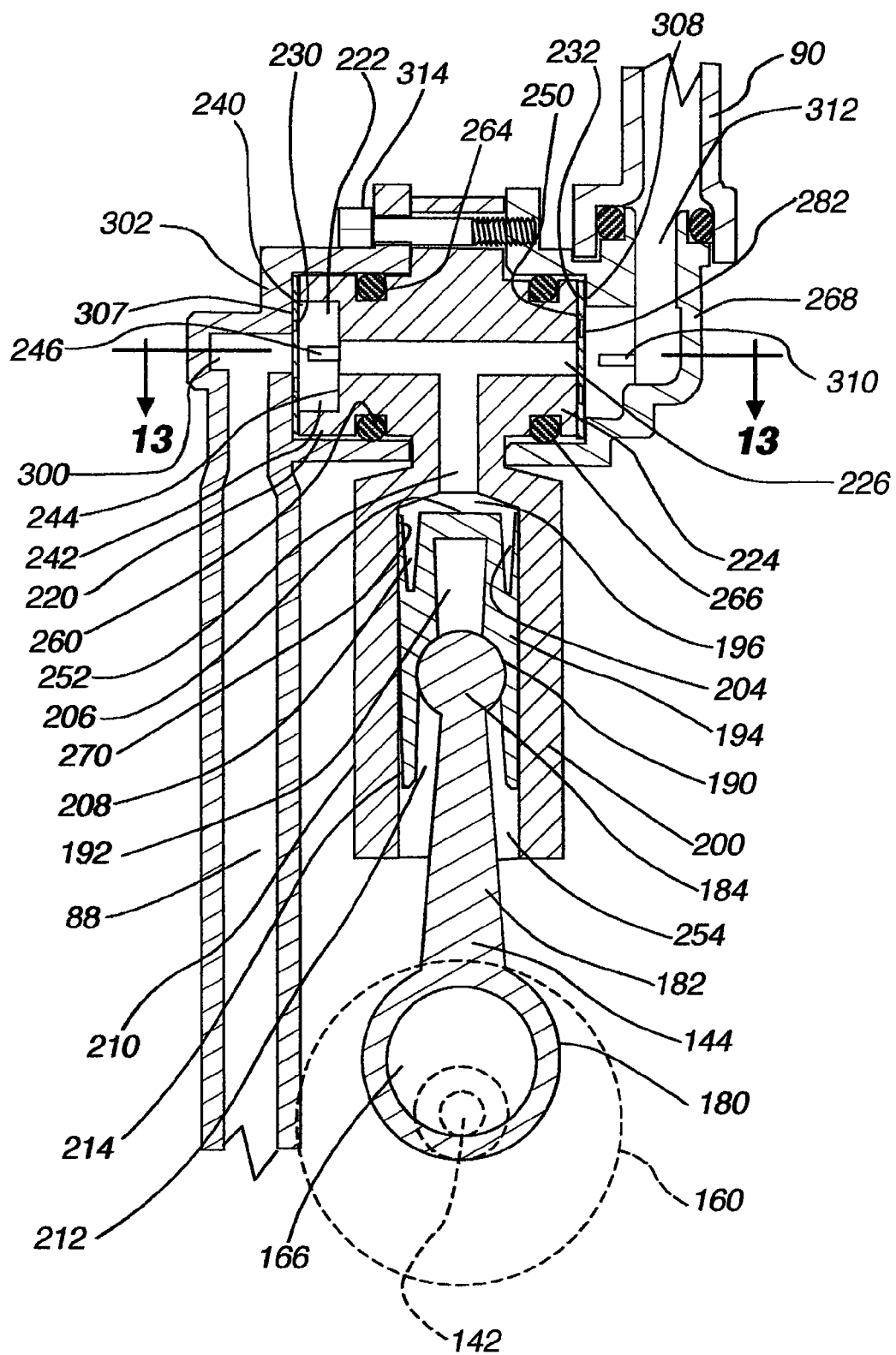
FIG. 10 illustrates a sectional view of the pump, in accordance with an embodiment of the present invention.

The connecting rod 144 of the drive mechanism 84 includes a hollow cylindrical portion 180 coupled with an arm 182 terminating at a ball end 184 (FIGS. 6, 24). The hollow cylindrical portion 180 encases the eccentric shaft/ offset disc 164, 166 of the pump gear 140 so as to receive the motion of the pump gear 140. In FIGS. 10 and 24, the ball end 184 of the connecting rod 144 is positioned within a curved, interior surface 190 of a recess 192 formed in a piston 194 that creates the pump 86. As the pump gear 140 rotates, the ball end 184 moves upwardly and downwardly and pivots within the recess 192 in the piston 194 as the piston 194 also moves in an upward and downward motion within a cylindrical chamber 196 of the pump 86. Hence, the connecting rod 144, attached to the piston 194 within the cylinder 196, converts the eccentric rotational movement of the offset disc 164 into linear movement and drives the piston 194 in an upward and downward motion within the cylinder 196 of the pump 86. The amount of offset distance 172 will affect the distance that the piston 194 travels within the pump body 200.

The piston 194 is sealed with the walls of the cylinder 196 but is also allowed to slide up and down in the cylinder 196 while maintaining the sealed relationship. In one example and referring to FIGS. 6 and 10, the piston 194 is generally cylindrical and has on its top surface 202 an annular flange 204 and an interior pedestal, an annular valley or recess 208 being defined between the annular flange 204 and pedestal 206. Within the pedestal 206, an interior cylindrical recess 192 is formed with a first inner diameter 210, with a second larger and convex inner diameter 212, increasing towards the lower end 214 of the piston 194. A curved interior surface 190 is provided within the interior cylindrical recess 192, between the first and second inner diameters 210, 212, for receiving the ball end 184 of the connecting rod 144 in order to form a ball joint.

Referring to FIGS. 6, 10–15, the pump 86 generally includes a pump head 220 and a pump body 200. The pump head 220 includes an inlet fluid port 222 and an outlet fluid port 224 each in fluid communications with an interior fluid channel 226. The pump body 200 defines a cylindrical chamber 196 in fluid communications with the interior fluid channel 226 of the inlet and outlet ports 222, 224. The pump 86 also includes a piston 194 and a pair of valves 230, 232 regulating the flow of fluid into and out of the inlet and outlet ports 222, 224.

The inlet fluid port 222 includes an outer ring or collar portion 240 defining an opening 242 terminating at an inner wall 244, the opening 242 having a diameter larger than the diameter of the interior fluid channel 226. The inlet port 222 also includes a protrusion 246 extending outwardly from the inner wall 244 but not extending beyond the outer ring/collar 240. In one example, the opening 242 is circular along a portion of its perimeter with a portion of its perimeter defining a straight ledge 248 (FIG. 6). The outlet fluid port 224 is defined, in one example, by a flat outer surface 250 centered about the interior fluid channel 226. A transverse fluid channel 252 (FIGS. 10–12) extends from the interior fluid channel 226 to the cylindrical chamber 196 of the pump body 200.

At one end, the cylindrical chamber 196 of the pump body 200 is in fluid communications with the interior fluid channel 226 of the pump head 220 via the transverse fluid channel 252. The opposing end 254 of the pump body is open so that the piston 194 can be inserted within the cylindrical chamber 196. As shown in FIG. 6, flanges 256, 258 extend outwardly and downwardly from the pump body 200 and act as support or securing members for securing the pump body 200 to the wall structure 120 or to the body 52.

Both the inlet and outlet ports 222, 224 of the pump 86 have annular grooves 260, 262 for receiving O-rings 264, 266 thereabout for forming fluid tight seals with the adjacent conduits 88, 90, 268 attached to the inlet and outlet ports 222, 224. In order to form a fluid tight seal between the piston 194 and the cylindrical chamber 196 within the pump body, the piston 194 is provided with a semi-hollow top portion 208 (FIGS. 10–12) that has an outer wall 270 which extends outwardly so that this top portion 208 of the piston 194 has an increasingly larger diameter when compared with the bottom portion 214 of the piston 194. In this way, the top portion 208 of the piston 194 forms a tight seal with the interior walls of the cylindrical chamber 196 of the pump body 200, while still permitting some clearance between the lower portion 214 of the piston and the interior walls of the cylindrical chamber 196 of the pump body 200.

In one embodiment, and as shown in FIGS. 6, 10–15, the pump 86 utilizes, on both its inlet and exhaust/outlet ports 222, 224, valves 230, 232, such as reed valves made from a flexible Teflon coated fiberglass tear-resistant, non-porous fabric material, such as Fluorofab 100-6 from Greenbelt Industries, which makes the pump assembly 86 simpler, lighter weight, smaller, and having less parts when compared with conventional spring-loaded valve assemblies. Further, the light weight nature of the reed valves 230, 232 also allows the valves to control/check the flow of fluid and air, thereby providing a reliable priming of the pump 86. The reed valves 230, 232 act as check valves which, when used as described herein, permit fluid to flow in only one direction. One or more reed valves 230, 232 may be used in hand held oral irrigator 50, or may also be useful for non-hand-held oral irrigators.

As shown in the example of FIG. 8, in one example a reed valve 230, 232 may include a flat piece of material with a rim 280 on a portion of its perimeter, a flap or tongue 282 with a rounded end 284 extending into the interior of the rim 280 forming a crescent shaped opening 286 between the flap 282 and the rim 280. A living hinge 288 is formed between the flap 282 and the rim 280, so that the flap 282 can move relative to the rim 280 about the hinge 288. A pair of stress/strain relief openings or slots 290 may be provided about the hinge 288 to reduce stress/strain on the hinge 288 as the flap 282 moves. A portion 292 of the perimeter of the reed valve 230, 232 may be straight, so as to fit within the inlet and outlet ports 222, 224 of the pump head 220 (FIG. 6) and ensure proper orientation within the pump 86.

As shown in FIGS. 10–12 and 13–15, the diameter of the flap 282 is selected so as to be greater than the diameter of the interior fluid channel 226 of inlet and outlet ports 222, 224 of the pump head 220. In this manner, the flaps 282 of the reed valves 230, 232 can fully seal closed the interior fluid channel 226 on either the inlet or outlet port 222, 224 during an exhaust or intake stroke of the pump 86. When the flap 282 of one of the reed valves 230, 232 is in an open position, fluid may pass through the reed valve by the flap 282 being displaced from the sealed position and through a portion of the crescent shaped opening 286 of the reed valve.

Figure 11:
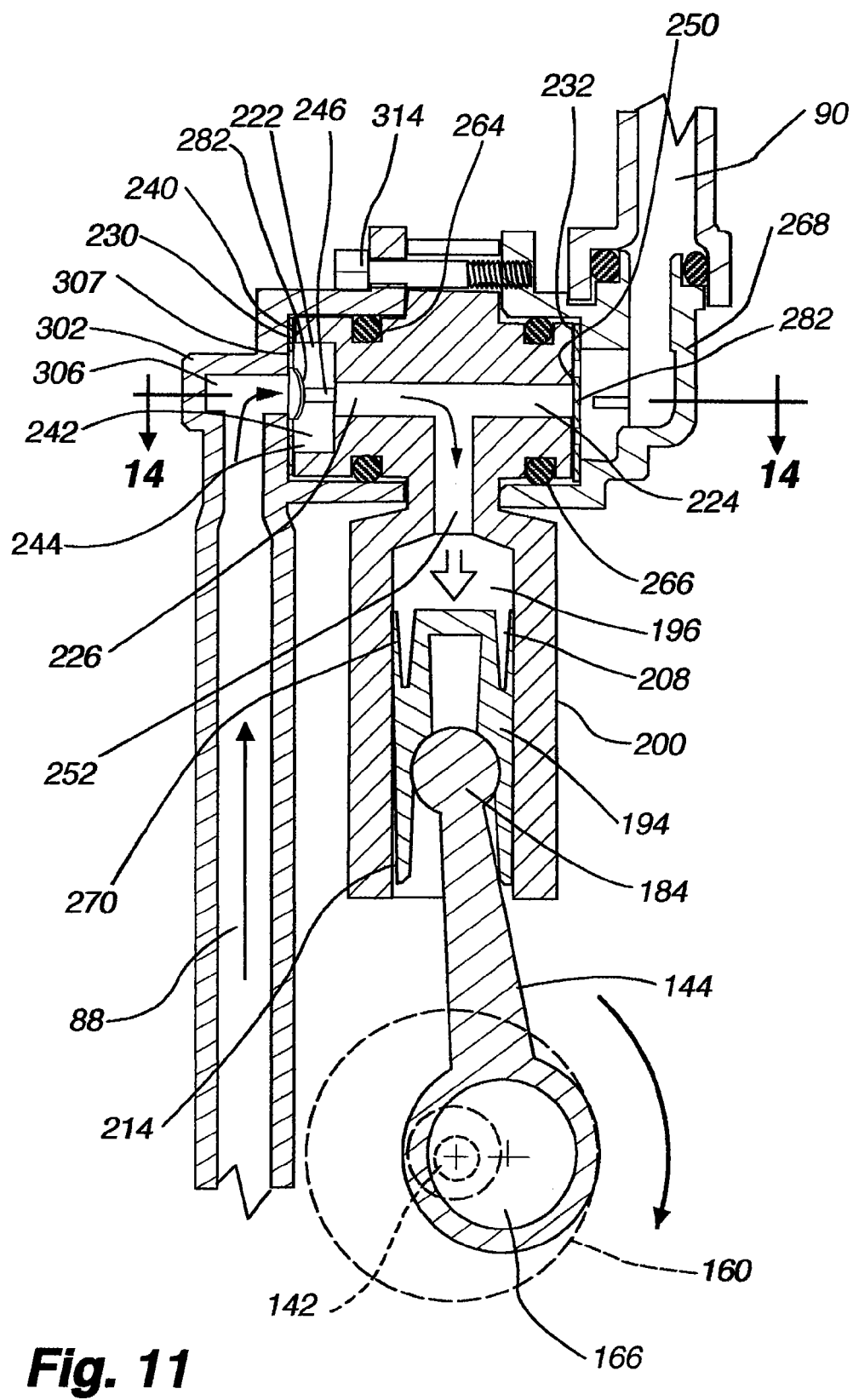
FIG. 11 illustrates a sectional view of the pump during an intake or suction stroke, in accordance with an embodiment of the present invention.
Figure 14:
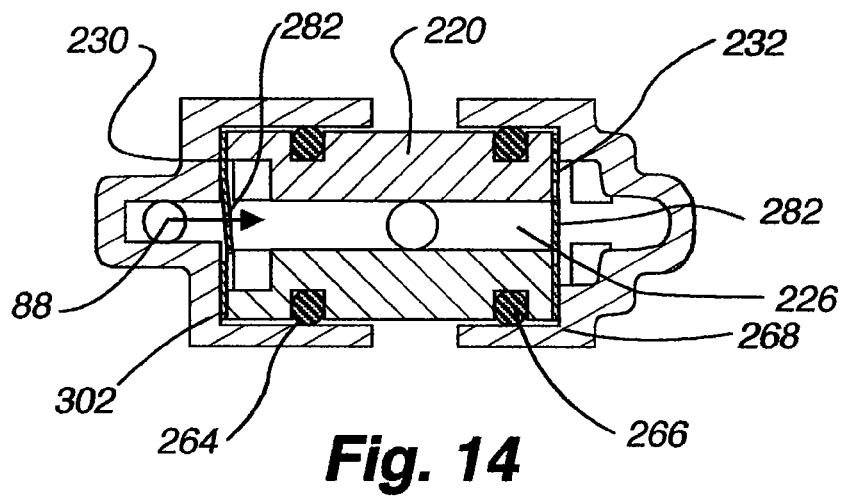
FIG. 14 illustrates a sectional view taken along section lines 14—14 of FIG. 11 showing the positions of the flaps of the reed valves during an intake or suction stroke, in accordance with an embodiment of the present invention.
Figure 15:
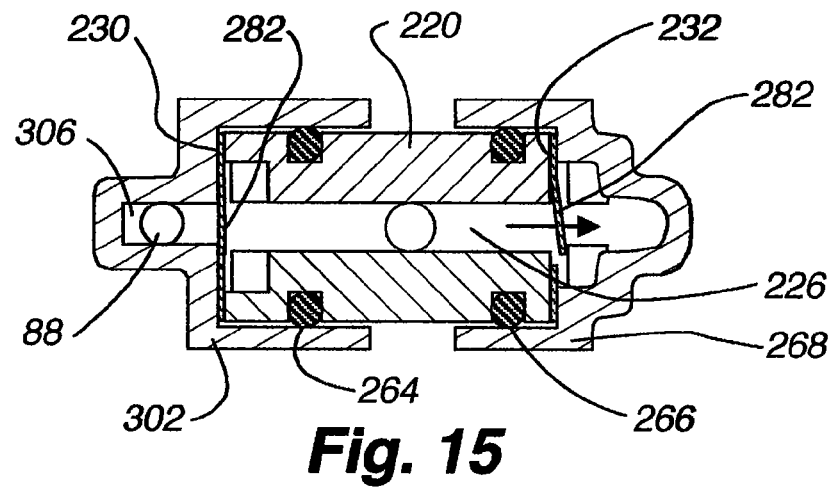
FIG. 15 illustrates a sectional view taken along section lines 15—15 of FIG. 12 showing the positions of the flaps of the reed valves during an exhaust or compression stroke, in accordance with an embodiment of the present invention.

In operation, when the piston 194 is moved downwardly within the pump body 200, this creates a suction stroke where fluid is drawn or sucked from the inlet port 222 past the opened inlet reed valve 230 into the cylindrical chamber 196 of the pump body 200 (FIGS. 11, 14). During the suction stroke, the outlet reed valve 232 is sealed shut because the diameter of the flap 282 is greater than the diameter of the interior fluid channel 226, and the flap 282 is drawn under suction toward the interior fluid channel 226 which creates a seal with the edges of the outer surface 250 of the outlet port 224. When the piston 194 is moved upwardly within the pump body 200, this creates a compression or exhaust stroke wherein the fluid within the cylindrical chamber 196 of the pump body 200 is expelled or pushed out of the pump body 200 through the outlet port 224 (FIGS. 12, 15) and past the opened outlet reed valve 232. During the exhaust stroke, the inlet reed valve 230 is sealed shut because the diameter of the flap 282 is greater than the diameter of the fluid channel 300 of the inlet cap 302 and the flap 282 is pushed outwardly to seal the inlet port 222.

Within the body 52 of the oral irrigator 50, a self-contained fluid flow path is defined, in one embodiment, by various conduits 88, 90 connected between the reservoir 54, pump 86 and tip 56. Referring to FIG. 6, a cylindrical pump inlet conduit 88 receives fluid from the reservoir 54 and is in fluid communications with the inlet port 222 of the pump 86 and the outlet port 224 of the pump 86, which is in fluid communications with an outlet conduit 90 which delivers fluid to an outlet joint 304 which is in fluid communications with the tip 56. The pump inlet conduit 88 provides a channel 306 through which fluid enters the inlet port 222 of the pump body 200 through the inlet reed valve 230 during a suction stroke. In one embodiment, the pump inlet conduit 88 has an inlet cap 302 that is coupled with and around the inlet port 222 and also houses the inlet reed valve 230 and an O-ring 264 to form a fluid-tight inlet port (FIGS. 6, 7, 10, 11). The inlet reed valve 230 is positioned between the interior walls 307 of the inlet cap 302 and the outer ring 204 of the inlet port 222. During a suction stroke, the flap 282 of the reed valve 230 moves inwardly until it contacts a protrusion 246 (FIGS. 7, 9, 10) which limits the inward movement of the flap 282 (thereby opening the fluid flow path and drawing fluid into the pump body 200), but during a compression or exhaust stroke, the flap 282 of the reed valve 230 cannot move outwardly from the pump body 200 and remains closed since the interior walls 307 of the inlet cap 302 limit the outward movement of the flap 282 (FIGS. 10, 11, 12, 14, 15).

The outlet reed valve 232 is positioned between the outer surface 250 of the outlet port 224 of the pump body 200 and the inner ledge surface 308 (FIG. 10) of the outlet cap 268. A protrusion 310 from the outlet cap 268 limits the maximum movement of the flap 282 of the outlet reed 232 valve during a compression or exhaust stroke such that the flap 282 of the reed valve 232 can move outwardly (thereby opening the fluid flow path into the outlet cap 268 and outlet conduit 90) but during a suction stroke, the flap 282 of the outlet reed valve 232 is sucked inwardly and its inward movement is limited by the outer surface 250 of the outlet port 224, hence the outlet port 224 remains closed, which prevents fluid from the outlet port 224 and outlet conduit 90 from being drawn into the pump body 200 (FIGS. 11, 12, 14, 15).

The outlet cap 268 defines an L-shaped fluid channel 312 therein and is coupled with a cylindrically shaped outlet conduit 90 (FIGS. 5, 7). Both the inlet cap 302 and the outlet cap 268 can be secured to the pump body 200 through a screw 314 as shown in FIGS. 6, 10. The outlet conduit 90 is fluidly coupled with an outlet joint 304 which is in fluid communications with the tip 56. In FIG. 24, a tip holding structure 320, with a U-322 positioned along its lower edge to form a seal between structure 320 and the interior of outlet joint 304, receives various tips 56 which can be inserted therein for delivering fluid to the user's teeth or gums.

Figure 16:
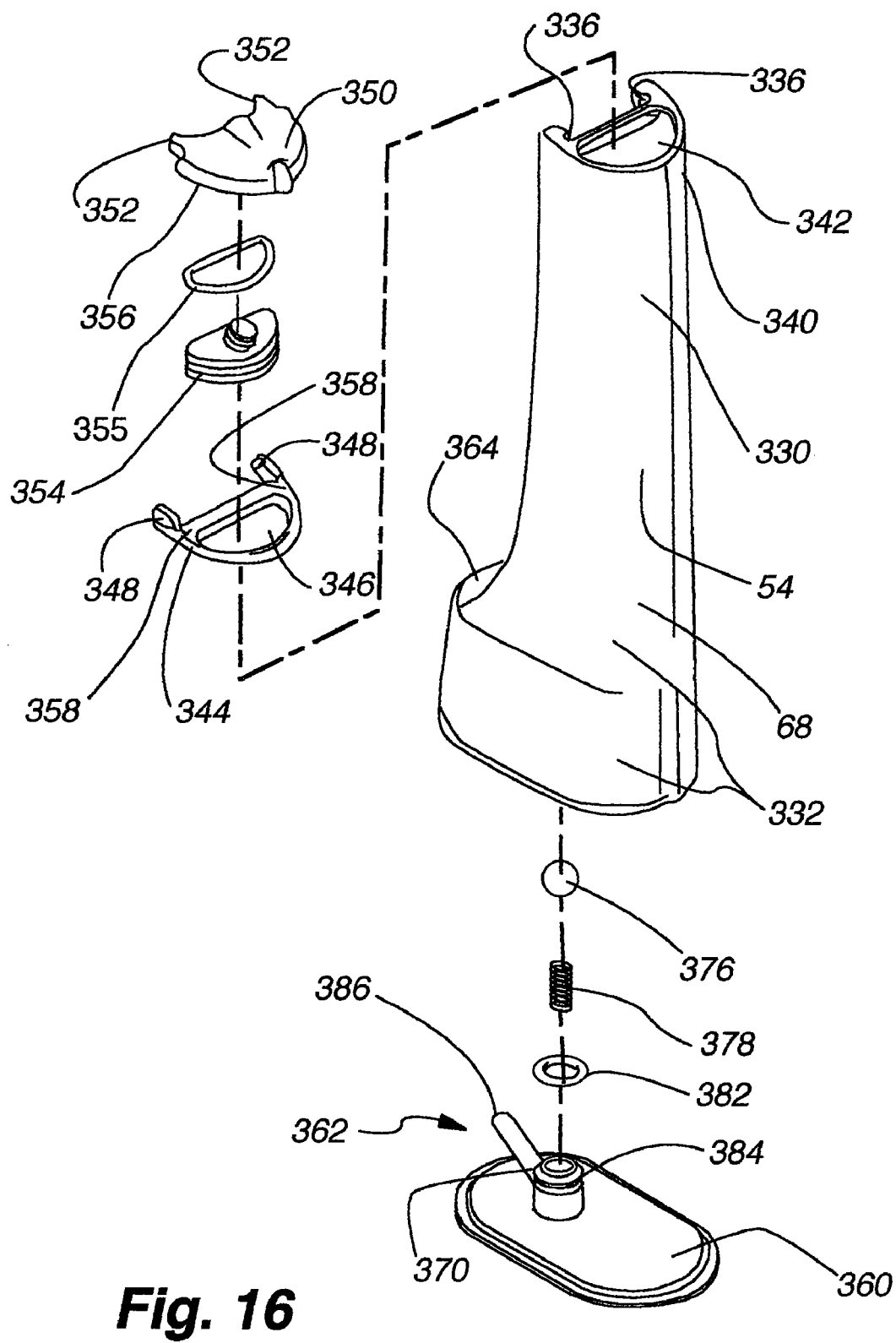
FIG. 16 illustrates an exploded view of the reservoir, in accordance with an embodiment of the present invention.

Referring now to FIGS. 16–21, a detachable, refillable reservoir 54 is illustrated in accordance with one embodiment of the present invention. As shown in FIG. 16, the reservoir 54 is generally elongated with a top portion 330 having a cross-section generally smaller than a cross-section of the bottom portion 332 of the reservoir 54. Due to this geometry, when the body 52 and reservoir 54 are connected together for operation, a user can easily hold the oral irrigator 50 in the user's hand about the top portion 330 of the reservoir 54.

In one example, the reservoir 54 may be removed from the body 52 of the oral irrigator 50 as the user desires, for instance, when the user wishes to refill the reservoir 54. Alternatively, the user may refill the reservoir 54 without disconnecting the reservoir 54 from the body 52.

On the interface portion 334 of the reservoir 54 (FIGS. 3, 16) adapted to contact or connect with the body 52, a pair of slots or grooves 336 are defined axially for slidably receiving the corresponding pair of parallel tongues or rails 338 (FIG. 5) extending from the body 52 of the oral irrigator 50. In one example, the top end 340 of the reservoir 54 is provided with an opening 342 for refilling the reservoir 54 with fluid such as water or other fluids. An end cap 344 with an opening 346 may be affixed to the top end 340 of the reservoir 54 and defines two pivot points or protrusions 348 about which a lid 350 with indentations 352 corresponding to the protrusions 348 can rotate upwardly or downwardly about the protrusions 348 as desired. A seal 354 with o-ring 355 can be affixed to the bottom portion 356 of the lid 350, or alternatively on the top portion of the opening 346, in order to sealably engage in the opening 346 of the end cap 344 so that when the lid 350 and seal 354 are in the closed position, a fluid tight seal is formed about the top end 340 of the reservoir 54 (FIG. 18). As shown in FIG. 16, one or more vent holes 358 are provided in the top of the reservoir end cap 344 in order to admit air into the reservoir 54 so that a vacuum is not created as fluid is pumped from the reservoir 54 through the tip 56.

Figure 21:
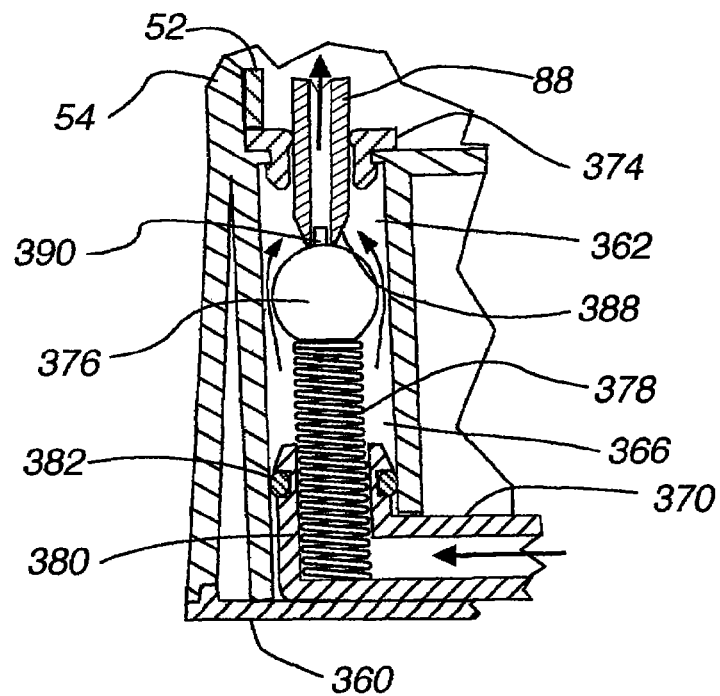
FIG. 21 illustrates a sectional view taken along section lines 21—21 of FIG. 20, showing the fluid access valve in an open position which permits fluid from the reservoir to enter into the pump inlet conduit of the body, in accordance with an embodiment of the present invention.

In one embodiment, the reservoir 54 is formed with a base 360 having a biased-closed fluid access valve 362 positioned on an interior shelf 364 of the reservoir 54 (FIGS. 16, 17, 19, 21). The fluid access valve 362 is normally closed and may be opened via contact with the pump inlet conduit 88 of the body 52 (FIG. 21). In one example, the fluid access valve 362 includes a vertically oriented cylindrical channel 366 defined within the reservoir 54 having an opening 367 at one end 368 for receiving a portion of a reservoir inlet conduit 370, and an opening 372 at the other end terminating on the interior shelf 364 of the reservoir 54 where a seal 374 with a cylindrical opening is positioned. Within the cylindrical channel 366, a ball 376 is pressed upwardly against the bottom of the seal 374 by a spring 378 which is maintained in position by an upwardly extending portion 380 of the reservoir inlet conduit 370 when positioned within the opening 367 of the cylindrical channel 366. An o-ring 382 is positioned about an annular recess 384 about the upwardly extending portion 380 of the reservoir inlet conduit 370.

When the reservoir 54 is separated from the body 52 of oral irrigator 50, the spring 378 presses the ball 376 against the seal 374 within channel 366, thereby preventing fluid from escaping reservoir 54.

Due to the positioning of the components of the fluid flow path within the reservoir 54 and the body 52, the pump 86 is self-priming which provides fast and rapid delivery of fluid stored in the reservoir 54 to the tip 56 during operation of the hand-held oral irrigator 50. The reservoir inlet conduit 370 is positioned on the base 360 of the reservoir 54 and defines an L-shaped fluid channel (FIG. 17) which receives fluid at its input 386 and guides, when the pump 86 is in suction mode, fluid to its upwardly extending portion 380 which is contained within the cylindrical channel 366. Accordingly, as the user fills the reservoir 54 with fluid, fluid immediately enters the input 386 of the reservoir inlet conduit 370, and as the fluid level within the reservoir 54 rises to above the level of the shelf 364, the fluid level within the cylindrical channel 366 also rises.

As shown in FIG. 21, when the body 52 of the oral irrigator 50 is slidably connected with the reservoir 54, the tip 388 of the pump inlet conduit 88 enters the opening 372 of the seal 374 and engages the ball 376 which compresses the spring 378 and allows fluid to enter the interior of the pump inlet conduit 88 through the slot 390 in the pump inlet conduit 88.

As the fluid level within the reservoir 54 is, for instance, at or near a full level, the fluid pressure formed by gravitational force or potential energy has a tendency to force the fluid upwards and out of the fluid access valve 362 whenever fluid access valve 362 is in an open position through contact with tip 388 of pump inlet conduit 88. Accordingly, when the reservoir 54 is at or near a full fluid level and the tip 388 of the pump inlet conduit 88 contacts and depresses the ball/spring 376, 378 of the fluid access valve 362, fluid flows upwardly into the inlet port 222 of the pump body 200 and primes the pump body 200 with fluid because the level of the fluid in the reservoir 54 is higher than the level of the inlet port 222 of the pump 86. This self priming effect occurs without reliance on the operation of the pump 86. When the user activates the oral irrigator 50 and the motor 82 activates the pump 86 to cycle between its suction and exhaust strokes, fluid is delivered to the tip 56 quickly and rapidly due to the fact that the pump 86 has been primed with fluid.

Figures 22, 23:
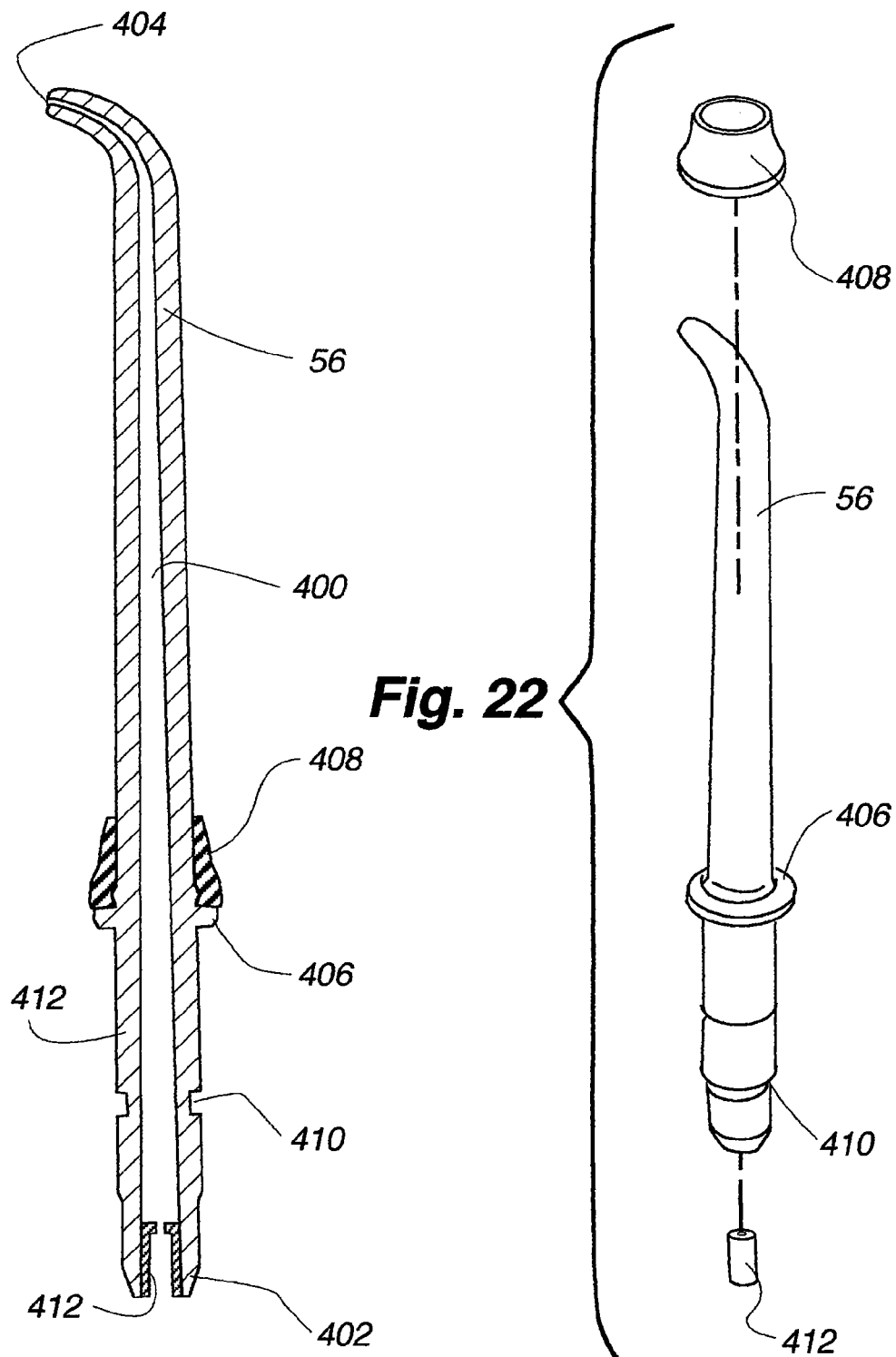
FIG. 22 illustrates an exploded view of a tip which may be used with the hand-held oral irrigator, in accordance with an embodiment of the present invention.
FIG. 23 illustrates a sectional view of the tip taken along section lines 23—23 of FIG. 3.

Various tips 56 can be detachably secured with the oral irrigator through the use of a tip release mechanism 92 illustrated in FIGS. 4, 24–26. One example of a tip 56 is illustrated in FIGS. 22–23, wherein the tip 56 is generally elongated with a cylindrical bore 400 through which fluid flows from the bottom 402 to the top 404 of the tip 56, and has an annular flange 406 upon which an identification or color-coded ring 408 rests which users may utilize to personalize or identify their tips 56. Further, a tip 56 may include an annular groove 410 defined in the lower portion 412 of the tip 56 which is used in combination with the tip release mechanism 92 for securely attaching the tip 56 to the body 52 of the oral irrigator 50. A restrictor 412 may be included within the bottom end 402 of the tip 56 for controlling the volume and rate of fluid flow through the tip 56. For instance, tips 56 having different sizes or differing restrictor 412 sizes may be provided with the oral irrigator 50 in order to permit the user to control the pressure at which the stream of fluid is delivered to the user's teeth or gums. For instance, in one example, a tip 56 characterized by an orifice size of 0.035 inches with a 0.030 inch diameter restrictor 412 has been found to provide pressure of approximately 64 psi, while in another example a tip 56 characterized by an orifice size of 0.026 inches with a 0.025 inch diameter restrictor 412 has been found to provide pressure of approximately 48–52 psi.

Figure 25:
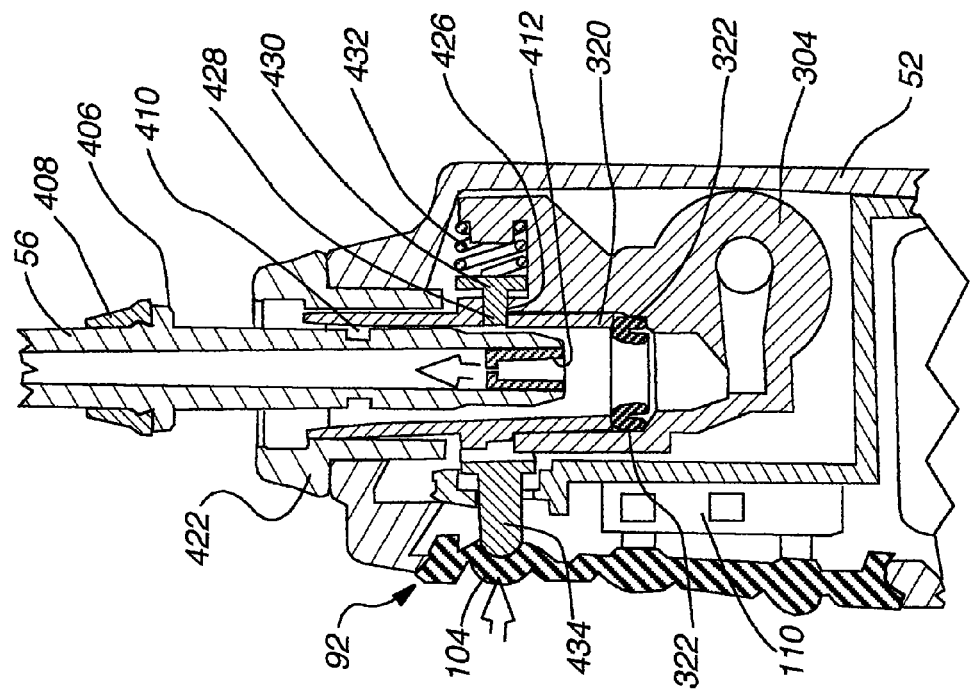
FIG. 25 illustrates a portion of a sectional view of the body portion of a hand-held oral irrigator showing the tip release button in the normally locked position, in accordance with an embodiment of the present invention.
Figure 26:
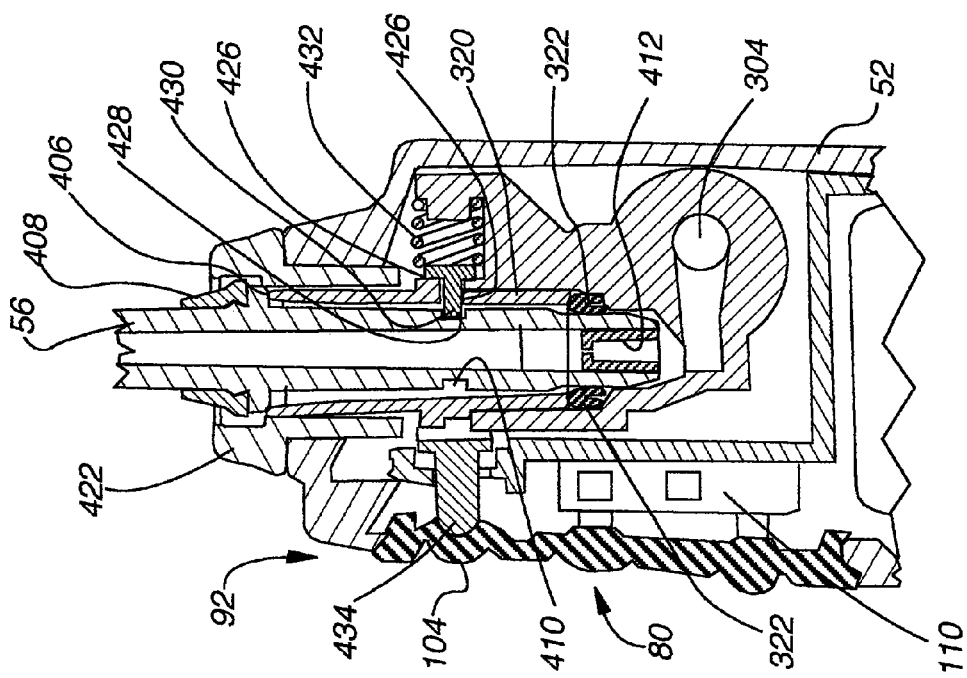
FIG. 26 illustrates a portion of a sectional view of the body portion of a hand-held oral irrigator showing the tip release button in the depressed, unlocked position, in accordance with an embodiment of the present invention.
Figure 28:
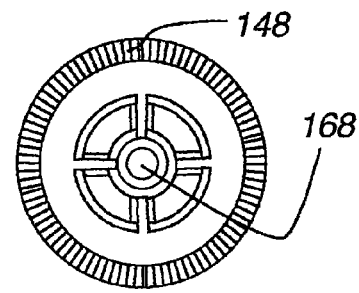
FIG. 28 illustrates a top view of a pump gear, in accordance with an embodiment of the present invention.

Referring now to FIGS. 24–26, the tip release mechanism 92 will now be described. The upper portion of the body 52 includes an opening 420 into which a tip control knob 422 is inserted which provides an interior surface 424 to engage and initially guide the tip 56 within the opening 420. The tip holding structure 320, which is generally cylindrical in shape, receives the bottom portion of the tip 56 as it is inserted into the body 52. In one example, the tip holding structure 320 includes an opening or slot 426 through a portion of its perimeter through which an interior lip 428 of a tip securing clip 430 may pass.

The tip securing clip 430 and spring 432 (FIGS. 5, 25, 26) are provided such that as a tip 56 is inserted into the opening 420 of the tip holding structure 320, the outer walls of the bottom portion of the tip 56 push outwardly on the lip 428 of the clip and compress the spring 432, and when the lower portion of the tip 56 is fully inserted into the opening 420 of the tip holding structure 320, the interior lip 428 of the clip 430 is received in the annular groove 410 of the tip 56 to provide the user with tactile and/or audible feedback that the tip has been completely and properly inserted in the body 52 (FIG. 25). The clip 430 is biased in this position under the force of the spring 432. Further, if the groove 410 is continuous around the tip 56, once the tip 56 has been fully inserted into the body 52, the tip 56 may be oriented or rotated as desired by the user.

When a user wishes to remove the tip 56 from the body 52, the user depresses a tip release button 104 (which is preferably part of the 3-way control structure 80) on the body 52 which pushes on a protrusion 434 of the tip securing clip 430, the protrusion 434 preferably located 180 degrees opposite the lip 428 of the clip 430. By moving the clip 430 towards the spring 432, the spring 432 is compressed which disengages the lip 428 of the clip 430 from the annular slot 410 of the tip 56 so that the tip 56 may be removed from the body 52 (FIG. 26).

In order to control the pressure of the fluid stream delivered to a user's teeth and gums, various tips 56 with differing orifice diameters may be used, with or without restrictors 412. For example, a jet tip 56 having orifice sizes of 0.026 inches for low-pressure (which may be used with a restrictor of 0.030 or 0.025 inch diameters, for example), 0.035 inches for low-pressure, or 0.026 inches for high-pressure, for example. A battery 100 (FIG. 4) such as a NiCad battery, such as a pair of 4/5SC NiCad rechargeable batteries, may be used, in one example. A charger 436 can be used to recharge the battery 100 in the oral irrigation device 50 through a door 438 which provides access to charger connection 128.

Reducing the motor speed may also reduce the pressure of the delivered fluid, and in one embodiment, the control 80 of FIG. 2 permits the user to select a low or high motor speed by correspondingly altering the voltage level applied to the motor. Furthermore, the offset 172 of the eccentric shaft 164, 166 used to drive the piston 194 (FIGS. 27–30) may also be selected to achieve a desired pressure or pulsation frequency. In one example, a 0.081 inch offset achieves a pulse rate of 1670 pulses/minute in a high frequency application and 1860 pulses/minute in a low frequency application, while a 0.091 inch offset achieves a pulse rate of 1750 pulses/minute in a high frequency application and 1920 pulses/minute in a low frequency application.

Pressure control may also be provided through the use of an adjustable valve located in the tip 56. In one example, a valve with a dial, such as a barrel valve, is provided in the tip 56 which permits a user to selectively adjust the pressure as the fluid stream passes through the valve in the tip 56, thereby regulating the overall pressure of the fluid as delivered by the oral irrigator 50.

By way of example only, an oral irrigator 50 may include a reservoir 54 having a capacity of approximately 120–200 ml (i.e., 150 ml), and delivering a flow rate of approximately 300 to 321 ml/minute when used with a high-pressure tip, resulting in approximately 30 seconds of irrigation when used with a full reservoir 54. Using a low pressure tip, the pressures may include 48–66 psi, in one example, resulting in approximately 27–35 seconds of irrigation when used with a full reservoir 54.

Figure 31:
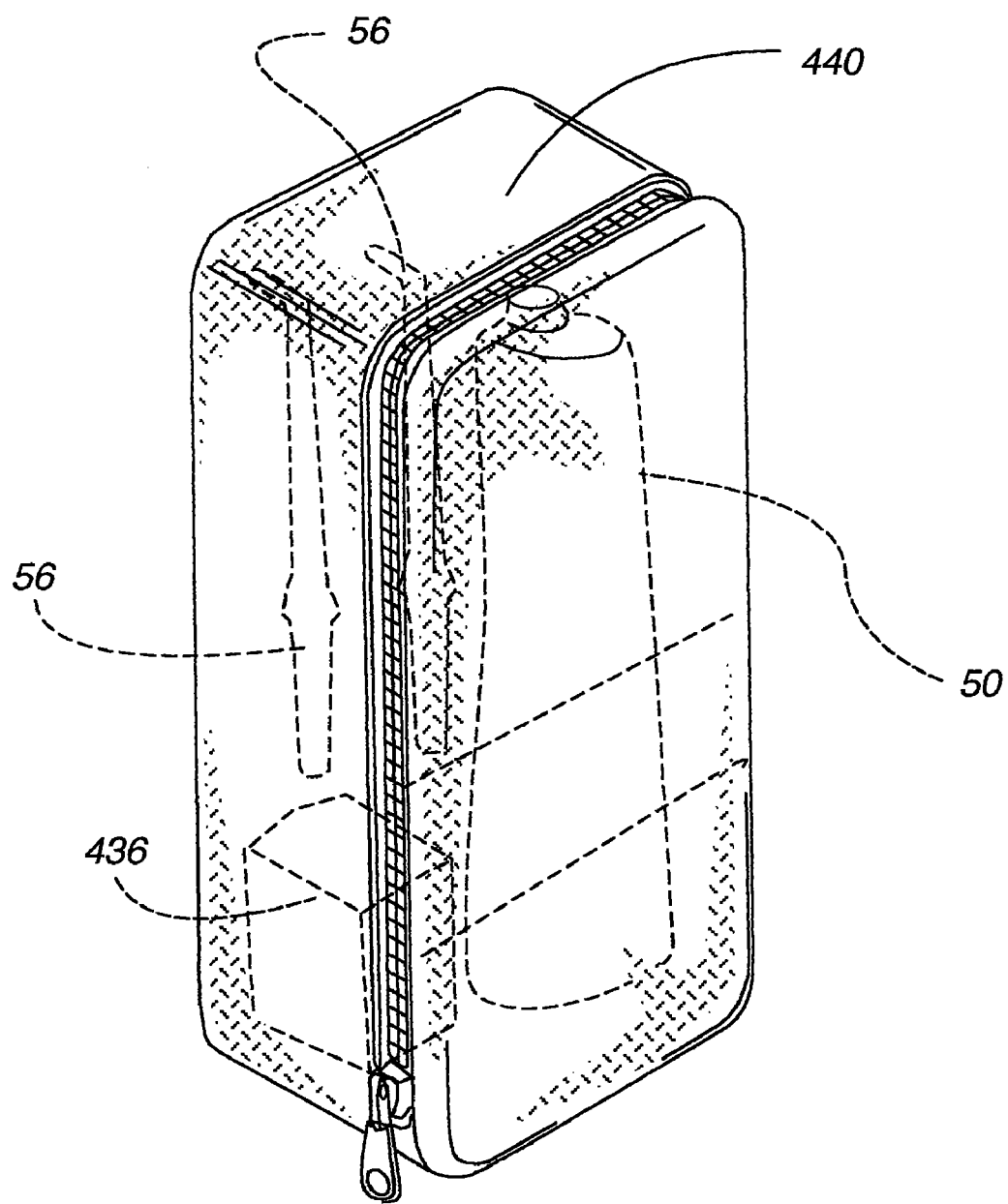
FIG. 31 illustrates an example of a travel case which may be used to store a hand-held oral irrigator, a battery charger, and one or more tips or other accessories, in accordance with an embodiment of the present invention.

Accordingly, as described above, it can be seen that various embodiments of the present invention may be used to form a hand held, portable oral irrigator with a detachable and refillable reservoir wherein various different tips may be attached to the oral irrigator. The compact and portable nature of embodiments of the present invention permit use of a travel case 440 (FIG. 31) to store and carry a hand held oral irrigator 50, a battery charger 442, and one or more tips 56 or other accessories in accordance with various embodiments of the present invention.

All directional references used herein (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention.

While the invention has been particularly shown and described with reference to various embodiments thereof, it will be understood by those skilled in the art that various other changes in the form and details may be made without departing from the spirit and scope of the invention.

What is claimed is:

1. A hand held oral irrigation device for irrigating an oral cavity with a fluid, the device comprising:
    a reservoir for storing the fluid;
    a body; and
    an elongated nozzle; wherein
    the reservoir comprises:
        a shelf portion defined about a bottom portion of the reservoir; and
        a base at a bottom end of the reservoir;
        a reservoir inlet conduit positioned along the base of the reservoir so that fluid is drawn from the bottom of the reservoir;
        a fluid access valve fluidly coupling with said inlet conduit, the fluid access valve comprising:
            a channel defined within the reservoir extending from the shelf to the base, said channel receiving said inlet conduit and fluidly coupled thereto;
            a seal positioned about a top end of the channel;
            a spring extending upwardly from the base within the reservoir; and
            a ball positioned within the channel between said seal and said spring;
        wherein the reservoir defines a first major diameter at a lower end of the oral irrigation device and the body and reservoir combine to define a second major diameter at an upper end of the oral irrigation device, the first major diameter being larger than the second major diameter.

2. The device of claim 1, wherein the body further comprises a motor, a pump, and a drive mechanism coupling the motor to the pump, said pump for controllably delivering the fluid from the reservoir to the nozzle.

3. The device of claim 2, further comprising:
    a three-way control structure having a first button for activating the motor, a second button for de-activating the motor, and a third button for releasing the nozzle from the body.

4. The device of claim 2, wherein the drive mechanism includes a pump gear coupled with said motor, wherein the pump gear includes an eccentric offset disc extending from said pump gear.

5. The device of claim 4, wherein the drive mechanism further comprises:
    a connecting rod coupled with the eccentric offset disc.

6. The device of claim 5, wherein the connecting rod further comprises:
    a hollow cylindrical portion receiving the eccentric offset disc of the pump gear;
    an arm extending from the cylindrical portion; and
    a bell end positioned at the end of said arm.

7. The device of claim 6, wherein the pump includes:
    a pump head having an inlet fluid port, an outlet fluid port, and an interior fluid channel in fluid communications with said inlet and outlet fluid ports;
    a pump body defining a cylindrical chamber in fluid communications with said interior fluid channel of said pump head; and
    a piston having a bottom portion and a top portion, the bottom portion receiving at one end the ball end of the connecting rod, said piston positioned within said cylindrical chamber of the pump body;
    wherein the inlet fluid port is fluidly coupled with the reservoir, and the outlet fluid port is fluidly coupled with the tip.

8. The device of claim 7, wherein the top portion of the piston includes:
    an annular flange;
    an interior pedestal; and
    an annular recess defined between the annular flange and the interior pedestal.

9. The device of claim 7, wherein the pump further comprises:
    an inlet fluid valve regulating fluid flow into said inlet fluid port; and
    an outlet fluid valve regulating fluid flow into said outlet fluid port.

10. The device of claim 9, wherein when the piston is moved downwardly within the cylindrical chamber of the pump body, the inlet fluid valve is open, the outlet fluid valve is closed, and fluid is drawn from the inlet port into the cylindrical chamber of the pump body.

11. The device of claim 10, wherein the first reed valve includes:
    a rim defined on a portion of a perimeter of the first reed valve;
    a hinge portion; and
    a flap portion interior to the rim, a first end of said flap portion attached to the hinge portion, said flap positioned relative to the rim so as to define a crescent shaped opening.

12. The device of claim 11, wherein the flap portion has a diameter, and wherein the interior fluid channel of the pump head has a diameter, the diameter of the flap portion being larger than the diameter of the interior fluid channel.

13. The device of claim 9, wherein when the piston is moved upwardly within the cylindrical chamber of the pump body, the inlet fluid valve is closed, the outlet fluid valve is open, and fluid is expelled from the cylindrical chamber of the pump body to the outlet fluid valve for delivery to the tip.

14. The device of claim 9, wherein the inlet fluid valve includes a first reed valve made of flexible fabric material.

15. The device of claim 9, wherein the outlet fluid valve includes a second reed valve made of flexible fabric material.

16. The device of claim 9, wherein the inlet fluid valve of the pump is vertically positioned within the body at a location lower than a full level of fluid in the reservoir, thereby self priming the pump with said fluid.

17. The device of claim 7, wherein the body further comprises:
    the inlet conduit fluidly coupling said reservoir with said inlet fluid port; and an outlet conduit fluidly coupling said outlet fluid port with said tip.

18. The device of claim 7, wherein the body further comprises the inlet conduit fluidly coupling said reservoir with said inlet fluid port.

19. The device of claim 2, wherein the body includes a wall structure defining a first and second section within the body, the first section containing the pump, and the second section contains the motor and the drive mechanism, wherein the first and second sections are fluidly isolated.

20. The device of claim 1, wherein the reservoir is detachable from the body.

21. The device of claim 1, wherein the reservoir has a top portion and a bottom portion, the top portion having a first cross section, the bottom portion having a second cross section, the second cross section being larger than the first cross section.

22. The device of claim 1, wherein the reservoir further comprises:

an opening positioned at a top end; and
a lid releasably secured about said opening.

23. The device of claim 1, wherein the reservoir has a capacity of approximately 120 to 200 ml of fluid.

24. The device of claim 1, wherein the nozzle further comprises an annular groove; and wherein the body further comprises:

a nozzle holding structure having a cylindrical wall defining a cylindrical opening;
a slot defined within said cylindrical wall;
a clip having an interior lip, said interior lip positioned within said slot and extending into said cylindrical opening; and
a spring for biasing the lip of the clip into the slot;
wherein when the spring is uncompressed, the lip is received within the annular groove of the nozzle to secure the nozzle to the body.

* * * * *